(12) United States Patent
Esfandiari

(10) Patent No.: US 9,476,875 B2
(45) Date of Patent: Oct. 25, 2016

(54) INTEGRATED BUFFER DUAL-PATH IMMUNOASSAY DEVICE

(71) Applicant: Chembio Diagnostic Systems, Inc., Medford, NY (US)

(72) Inventor: Javanbakhsh Esfandiari, Stony Brook, NY (US)

(73) Assignee: CHEMBIO DIAGNOSTIC SYSTEMS, INC., Medford, NY (US)

( * ) Notice: Subject to any disclaimer, the term of this patent is extended or adjusted under 35 U.S.C. 154(b) by 80 days.

(21) Appl. No.: 14/636,103

(22) Filed: Mar. 2, 2015

(65) Prior Publication Data

US 2016/0258943 A1  Sep. 8, 2016

(51) Int. Cl.
  *G01N 33/48* (2006.01)
  *G01N 33/543* (2006.01)
  *B01F 11/00* (2006.01)

(52) U.S. Cl.
  CPC .. *G01N 33/54386* (2013.01); *G01N 33/54366* (2013.01); *B01F 11/0071* (2013.01)

(58) Field of Classification Search
  CPC .. G01N 33/76; G01N 33/538; G01N 33/558; G01N 33/5695
  See application file for complete search history.

(56) References Cited

U.S. PATENT DOCUMENTS

| | | |
|---|---|---|
| 4,956,275 A | 9/1990 | Zuk et al. |
| 4,960,691 A | 10/1990 | Gordon et al. |
| 4,965,047 A | 10/1990 | Hammond |
| 5,489,414 A | 2/1996 | Schreiber et al. |
| 5,641,639 A | 6/1997 | Perry |
| 5,648,047 A | 7/1997 | Kardish et al. |
| 5,686,315 A | 11/1997 | Pronovost et al. |
| 5,714,380 A | 2/1998 | Neri et al. |
| 5,726,010 A | 3/1998 | Clark |
| 5,726,013 A | 3/1998 | Clark |
| 5,750,184 A | 5/1998 | Imburgia |
| 5,756,049 A | 5/1998 | Brayton |
| 5,804,141 A | 9/1998 | Chianese |
| 5,830,344 A | 11/1998 | Priddy et al. |
| 5,989,921 A | 11/1999 | Charlton et al. |
| 6,001,658 A | 12/1999 | Fredrickson |
| 6,004,820 A | 12/1999 | Brayton |
| 6,077,711 A | 6/2000 | Singer |
| 6,090,347 A | 7/2000 | Emodi |
| 6,159,747 A | 12/2000 | Hartig et al. |
| 6,165,416 A | 12/2000 | Chandler |
| 6,234,310 B1 | 5/2001 | Goldhaber |
| 6,303,288 B1 | 10/2001 | Furcht et al. |
| 6,391,260 B1 | 5/2002 | Davis et al. |
| 6,451,606 B1 | 9/2002 | Konig et al. |
| 6,541,994 B2 | 4/2003 | Masuda |
| 6,548,018 B2 | 4/2003 | DiCesare et al. |

(Continued)

*Primary Examiner* — Minh N Tang
(74) *Attorney, Agent, or Firm* — Gordon & Jacobson, P.C.

(57) ABSTRACT

A test device for use with a liquid solution includes a housing that houses a plurality of sorbent strips. At least one strip has a location for receiving the solution. The housing defines at least an opening in said housing wherein said opening is aligned with the location for receiving the solution. The device includes a sealed reservoir filled with the liquid solution, the sealed reservoir being disposed in alignment with the opening and coupled to the housing. The device includes an opener coupled to the housing. The opener is arranged to rotate from a first position, in which the opener is not in contact with the sealed reservoir, to a second position, in which the opener causes the sealed reservoir to effect a release of the solution from the reservoir and into the opening and onto the sorbent strip housed within the housing.

21 Claims, 29 Drawing Sheets

(56) References Cited

U.S. PATENT DOCUMENTS

| | | |
|---|---|---|
| 6,656,741 B1 | 12/2003 | Nelson et al. |
| 6,861,259 B2 | 3/2005 | Columbus |
| 6,887,709 B2 | 5/2005 | Leong |
| 6,938,757 B2 | 9/2005 | Eastman et al. |
| 7,090,803 B1 | 8/2006 | Gould et al. |
| 7,132,078 B2 | 11/2006 | Rawson et al. |
| 7,189,522 B2 | 3/2007 | Esfandiari |
| 7,332,348 B2 | 2/2008 | Sandell |
| 7,465,587 B2 | 12/2008 | Imrich |
| 7,473,397 B2 | 1/2009 | Griffin et al. |
| 7,517,495 B2 | 4/2009 | Wu et al. |
| 7,591,791 B2 | 9/2009 | Keren |
| 7,625,760 B2 | 12/2009 | Kitaguchi et al. |
| 7,638,093 B2 | 12/2009 | Wang et al. |
| 7,749,453 B2 | 7/2010 | Rannikko et al. |
| 7,935,318 B2 | 5/2011 | Harding |
| 7,939,021 B2 | 5/2011 | Smith et al. |
| 8,003,060 B2 | 8/2011 | Cracauer et al. |
| 8,110,392 B2 * | 2/2012 | Battrell ............... B01F 11/0071 427/2.11 |
| 8,273,312 B2 | 9/2012 | Porat et al. |
| 8,278,091 B2 | 10/2012 | Rutter et al. |
| 8,394,336 B2 | 3/2013 | Curcio |
| 8,441,629 B2 | 5/2013 | Kolesnychenko et al. |
| 8,506,908 B2 | 8/2013 | Benn et al. |
| 8,512,637 B2 | 8/2013 | Zeijlstra et al. |
| 8,628,730 B2 | 1/2014 | Sandell |
| 8,641,971 B2 | 2/2014 | Van Doorn et al. |
| 2001/0008774 A1 | 7/2001 | May et al. |
| 2004/0184954 A1 | 9/2004 | Guo et al. |
| 2009/0181411 A1 | 7/2009 | Battrell et al. |
| 2013/0309760 A1 * | 11/2013 | Raj ................ G01N 33/54366 435/287.7 |
| 2015/0056688 A1 | 2/2015 | Esfandiari |

* cited by examiner

TB STAT-PAK II vs. NEW GENERATION TB ASSAY

SAMPLES: TBGL CONTROLS

| | TB STAT-PAK™ II | NEW GENERATION |
|---|---|---|
| 32 U/ml | +++ | +++ |
| 8 U/ml | ++ | ++ |
| 2 U/ml | +/− | + |
| 1 U/ml | − | + |
| 1/2 U/ml | − | + |
| 1/4 U/ml | − | + |
| 1/8 U/ml | − | − |
| 0 U/ml | − | − |

NOTE: DILUTIONS ≤ 1 U/ml WERE MADE FROM 2 U/ml SAMPLE

FIG.11

LABORATORY RESULT FOR THE NEW GENERATION HIV TEST

|  | DILUTION | NG HIV TEST | HIV STAT-PAK™ |
|---|---|---|---|
| HIV-1 | 1:64 | 3 | 3 |
|  | 1:128 | 3 | 2 |
|  | 1:256 | 3 | 3 |
|  | 1:512 | 2 | 2 |
|  | 1:1024 | 1 | 1 |
|  | 1:2048 | 1 | N |
|  | 1:4096 | 1 | N |
|  | 1:8192 | N | N |
| HIV-2 | 1:4 | 3 | 3 |
|  | 1:8 | 3 | 3 |
|  | 1:16 | 3 | 2 |
|  | 1:32 | 2 | 2 |
|  | 1:64 | 2 | 1 |
|  | 1:128 | 2 | 1 |
|  | 1:256 | 2 | N |
|  | 1:512 | 1 | N |
|  | 1:1024 | N | N |
|  | 1:2048 | N | N |

INTENSITY      RESULT

1 — WEAK POS
2 — MEDIUM POS
3 — STRONG POS
N — NEGATIVE

FIG.12

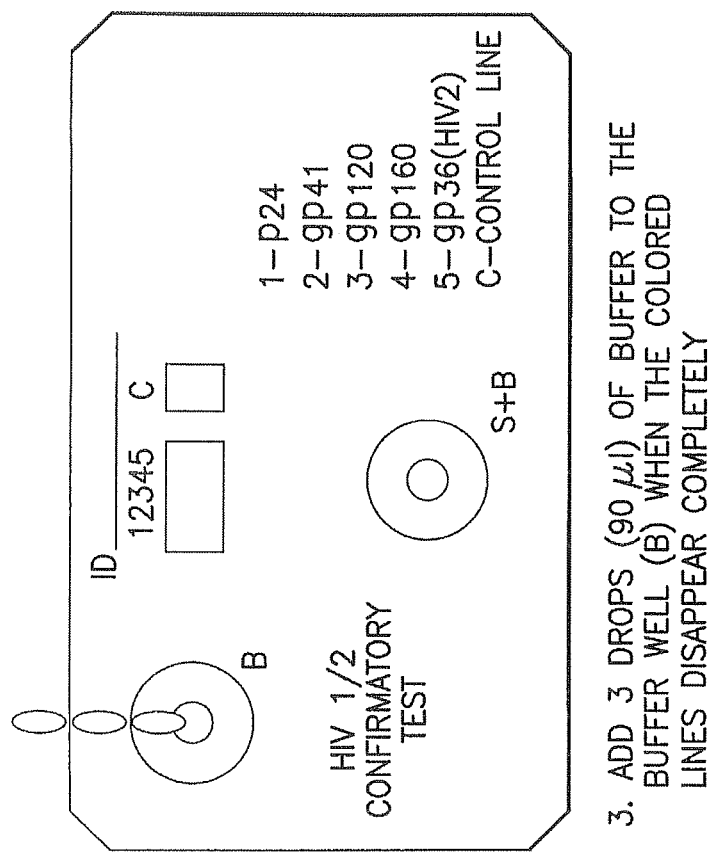

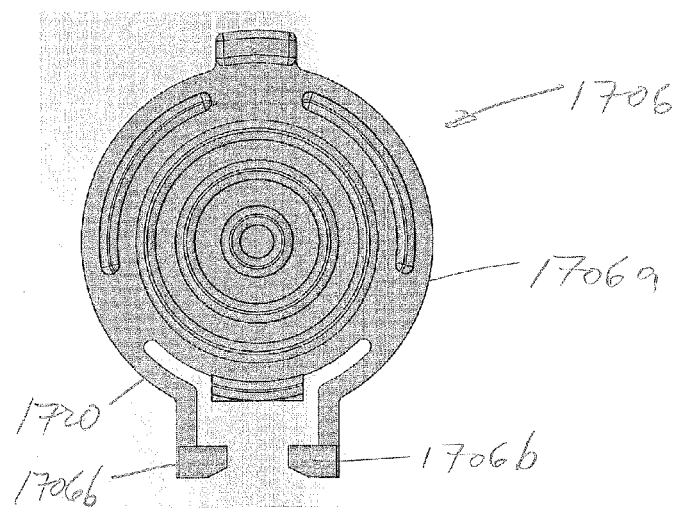
FIG. 17A
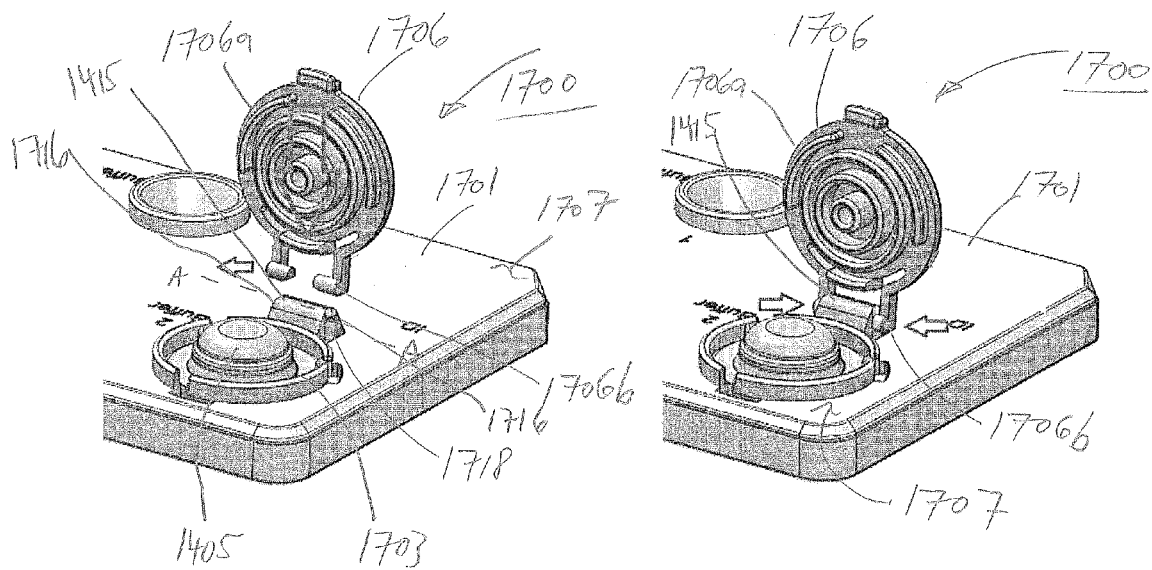
FIG. 17B
FIG. 17C

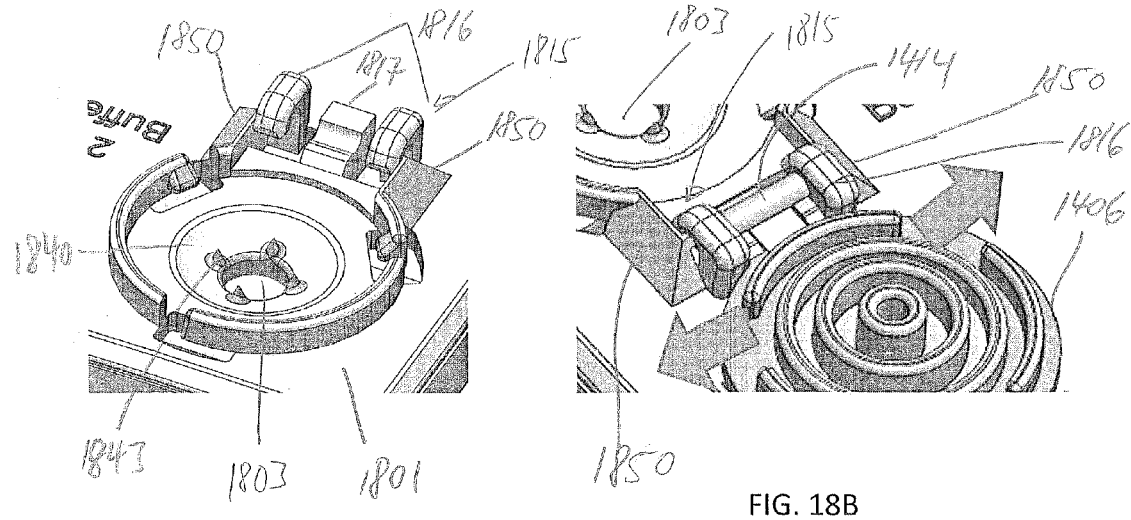
FIG. 18A
FIG. 18B
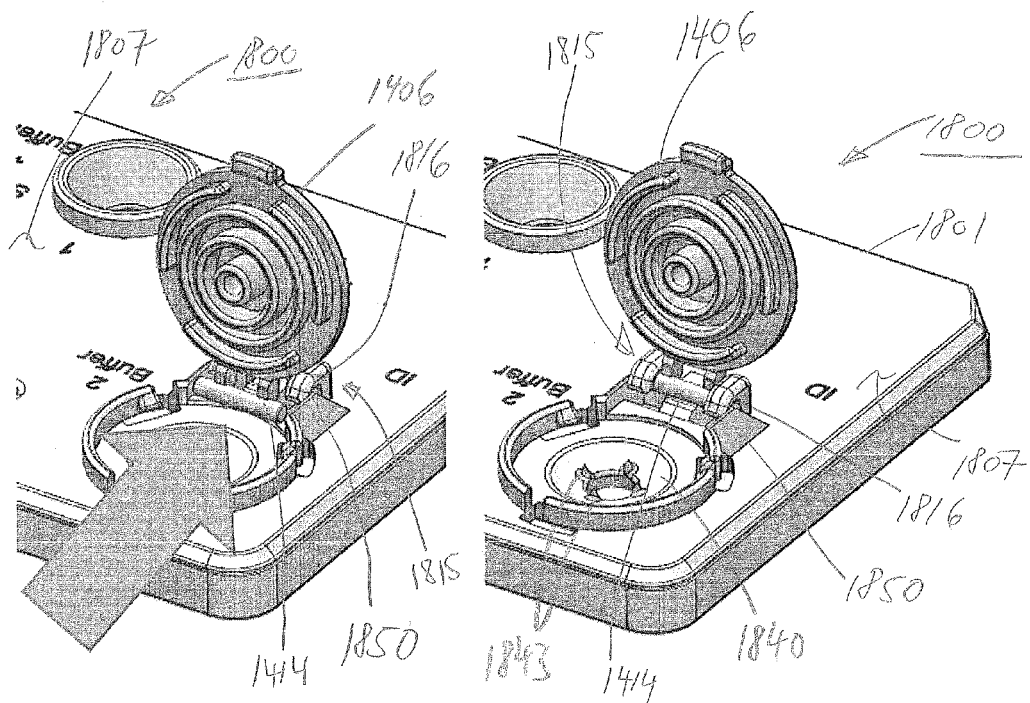
FIG. 18C
FIG. 18D

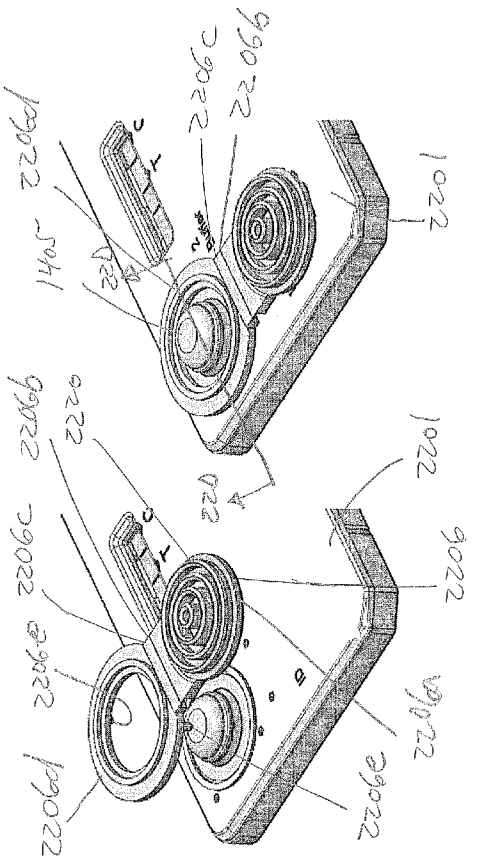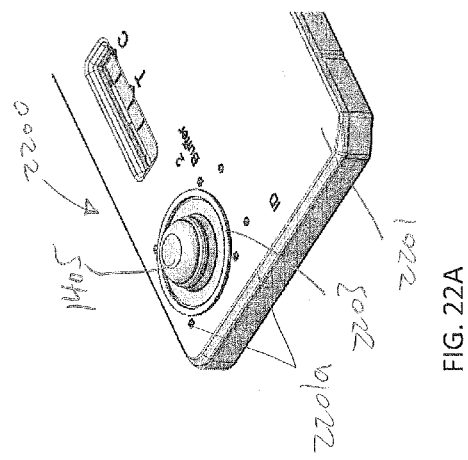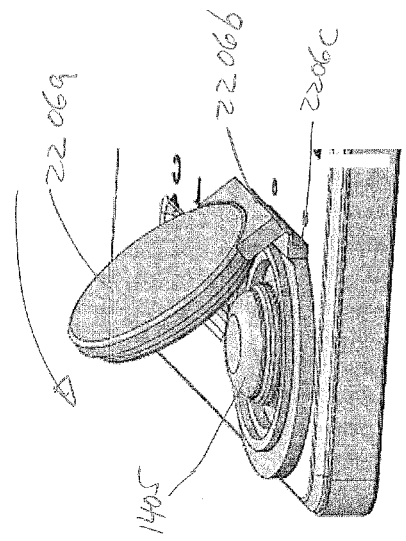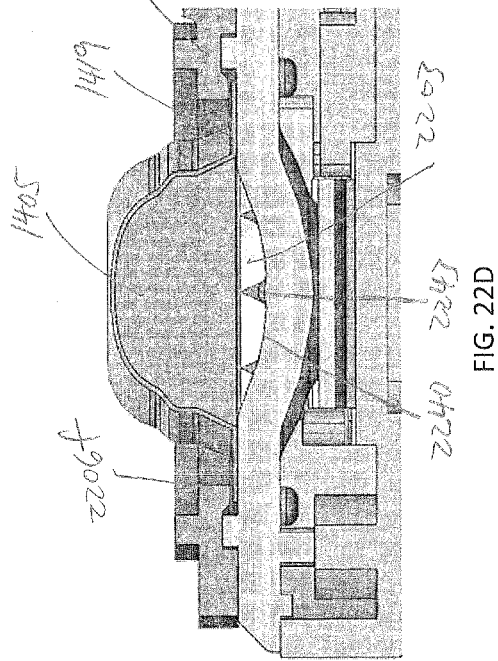
FIG. 22A  FIG. 22B  FIG. 22C  FIG. 22D  FIG. 22E

INTEGRATED BUFFER DUAL-PATH IMMUNOASSAY DEVICE

CROSS-REFERENCE TO RELATED APPLICATIONS

This application is related to U.S. Pat. No. 7,189,522, granted Mar. 13, 2007, the entire contents of which are incorporated herein by reference.

BACKGROUND

1. Field

The present invention relates to immunoassay devices and the methods for their use.

2. State of the Art

U.S. Pat. No. 7,189,522 relates to a dual path immunoassay device for use with a solution and for use with a conjugate having a marker. The test device is for determining the presence of a ligand in a sample.

Generally, the solution used in conjunction with the immunoassay device is a liquid that is dispensed from a bottle that is separate from the device. For example, a buffer solution may be dispensed from a squeeze bottle which may dispense drops of the solution through an opening in a housing of the device. Typically, to perform a test using the device, a user first injects or inserts the sample through one opening in the housing and then squeezes a certain number of drops (e.g., 3 drops) from the bottle into another opening in the housing. Such manual dispensing by the user may introduce errors into the testing if too much or too little buffer solution is introduced through the other opening. For example, if the bottle is held at an angle instead of being held vertically with respect to the housing, the amount of buffer in each drop may be different and, therefore, may affect the test results.

SUMMARY

In a first aspect, a test device, such as the aforementioned dual path lateral flow test device described in U.S. Pat. No. 7,189,522 includes an integrated solution reservoir that is filled with a fixed quantity of solution. The integrated reservoir can be opened and drained when a test is run to dispense the quantity of the solution into the device. As a result, the aforementioned solution measurement uncertainty may be mitigated or eliminated.

More specifically, according to one aspect, a test device for use with a liquid solution includes a housing that houses a plurality of sorbent strips. At least one strip has a location for receiving the solution. The housing defines at least an opening in the housing wherein said opening is aligned above the location for receiving the solution. The device includes a sealed reservoir filled with the liquid solution, the sealed reservoir being disposed in alignment with and over the opening and coupled to the housing. The device includes a reservoir opener coupled to the housing. The opener is arranged to rotate from a first position, in which the opener is not in contact with the sealed reservoir, to a second position, in which the opener crushes the sealed reservoir to effect a release of the solution from the reservoir and into the opening and onto the sorbent strip housed within the housing.

Also, in at least one embodiment a test device for use with a solution and for use with a conjugate having a marker is provided. The test device is for determining the presence of a ligand in a sample. The test device includes a first sorbent strip having a first location for receiving the solution and defining a first migration path for the solution and the conjugate; a second sorbent strip distinct from the first sorbent strip having a second location for receiving the sample and defining a second migration path for the sample distinct from the first migration path; and a test site located on or in at least one of the first sorbent strip or the second sorbent strip. The test site has an immobilized ligand-binding mechanism, and the first and second sorbent strips touch each other at the test site.

Also, the test device includes a housing that houses the first and second sorbent strips. The housing defines a first opening aligned with the first location, a second opening aligned with the second location, and a window aligned with the test site and through which the test site is viewable.

Further, the test device includes a sealed reservoir filled with the solution. The sealed reservoir is disposed in alignment with the first opening and is coupled to the housing. In addition, the test device includes a reservoir opener coupled to the housing. The opener is arranged to rotate from a first position in which the opener is not in contact with the sealed reservoir and is arranged to rotate to a second position in which the opener pierces the sealed reservoir to release the solution into the first opening and onto the first sorbent strip.

Additional aspects and associated advantages will become apparent to those skilled in the art upon reference to the detailed description taken in conjunction with the provided figures.

BRIEF DESCRIPTION OF THE DRAWINGS

FIG. 11 is a table showing a comparison of the sensitivity of the test device of the invention relative to a typical prior art TB test device.

FIG. 12 includes two tables and a key, with the tables showing comparisons of the sensitivity of the test device of the invention relative to typical prior art HIV1 and HIV2 test devices.

FIGS. 13A to 13G are composite photograph/instructional diagrams of an HIV 1/2 test cassette product, shown without an opener, and showing a procedure of utilizing the test product, and FIGS. 13D to 13G showing various possible test results.

FIGS. 17A to 17C illustrate another alternate embodiment to that shown in FIGS. 15A and 15B.

FIGS. 18A to 18D illustrate yet another alternate embodiment to that shown in FIGS. 15A and 15B.

FIGS. 22A to 22E illustrate an alternative embodiment to that shown in FIGS. 21A to 21D in which a living hinge is attached to a mounting ring which secures a sealed reservoir to the test cassette.

DETAILED DESCRIPTION

Figure 1:
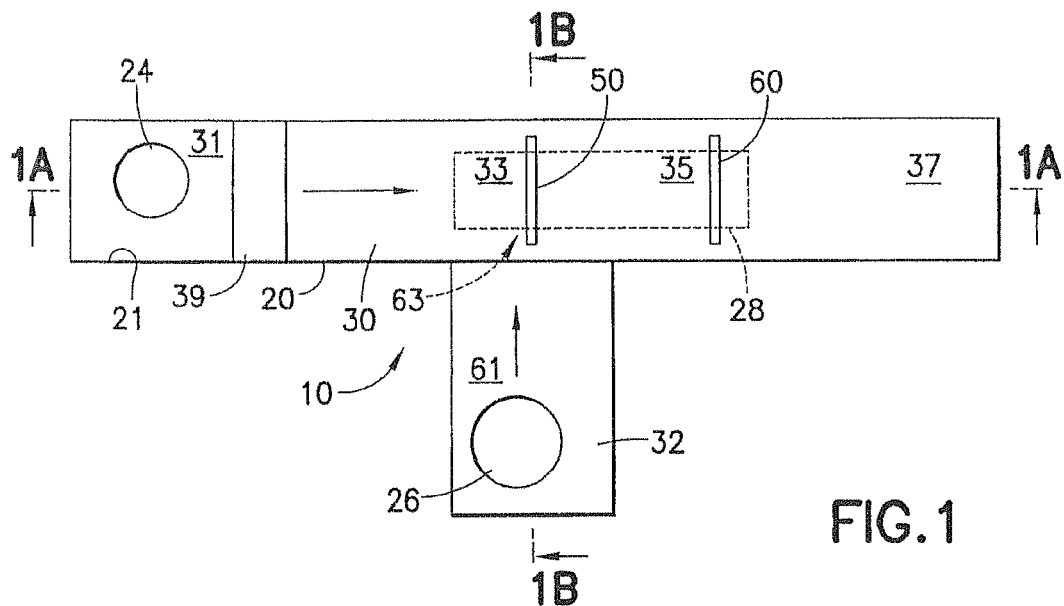
FIG. 1 is a top schematic view of a first embodiment of the invention, shown without an opener.
Figure 1A:
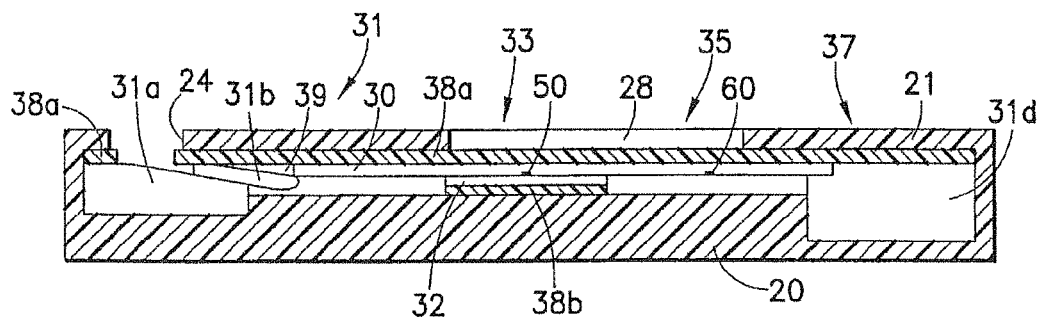
FIG. 1A is a cross-sectional view taken along line 1A-1A of FIG. 1, shown without an opener.
Figure 1B:
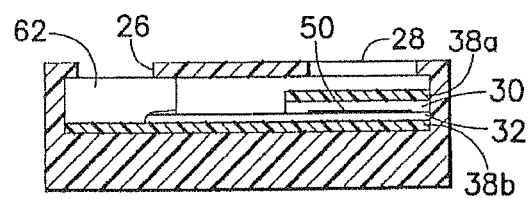
FIG. 1B is a cross-sectional view taken along line 1B-1B of FIG. 1, shown without an opener.

Turning now to FIGS. 1, 1A, and 1B, an immunoassay device test cell 10 is provided and includes: a T-shaped housing 20 having a top wall 21 defining first and second holes 24, 26, and a window 28; and first and second sorbent or bibulous materials 30, 32 defining perpendicular horizontal flow paths in the housing. The first sorbent material 30 includes at least two and perhaps three or four zones and may be made from a plurality of materials. A first zone 31 (sometimes called a filter zone) is located at the first hole 24 and extends to a second zone 33 (sometimes called a test zone) which is located at the junction of the "T". The first zone 31 may include a filter 31a, a pad 31b on or in which a conjugate 39 having desired antigens or antibodies with attached colored markers is deposited and immobilized, and a first portion of a thin membrane or sorbent or bibulous material 30 typically made from nitrocellulose with a plastic backing (not shown). The first zone 31 is adapted to receive a buffer solution, to cause the buffer solution to contact the conjugate, thereby mobilizing the conjugate, and to wick the conjugate-carrying buffer solution to the second zone 33. The second (test) zone 33 includes a second portion of the thin membrane 30 which can be printed with a test line 50 having immobilized antigens or antibodies (depending on whether the test cell is designed to test for the presence of antibodies or antigens) on the membrane as is well known in the art. The test line 50 may be seen through the window 28 of clear plastic provided in the housing. An optional third zone 35 (sometimes called a control zone) which includes a third portion of the thin membrane 30 may also be printed with a control line 60 typically containing antibodies to the conjugate antigens (or in some cases antibodies which will bind to conjugate antibodies, or even antigens which will bind to conjugate antibodies) as is well known in the art. Where the third zone 35 is provided, window 28 extends above the control line 60. If desired, an optional fourth zone 37 (sometimes called a reservoir zone) may be provided as a wicking reservoir as is also well known in the art. The fourth zone 37 includes a relatively thicker absorbent paper 31d. Overlying all the zones may be a thin, preferably transparent plastic film or card 38a having an adhesive which keeps the sorbent materials in place. The card 38a may be cut with an opening at hole 24 so that it does not block liquid access to the hole 24.

The second sorbent material 32 may also be made from a plurality of materials and may include two zones 61, 63. The first zone 61 (sometimes called a filter zone) includes a filter or pad 62 and a first portion of a thin membrane or sorbent or bibulous material 32 typically made from nitrocellulose with a backing (not shown). The first zone 61 is located at the second hole 26 and extends to the second zone 63. The second zone 63 includes a second portion of the thin membrane 32 which is in contact with the second zone 33 of the first sorbent material 30. As is seen in FIGS. 1A and 1B, the first sorbent material 30 overlies the second sorbent material 32 such that the membranes are in contact with each other (as opposed to the backings contacting the membranes or each other), and such that the test line 50 is effectively located between the membranes. Thus, test line 50 could be printed on the second zone 63 of the second sorbent material 32 instead of, or in addition to the second zone 33 of the first sorbent material 30. If desired, a thin plastic film or card 38b having an adhesive which keeps the second sorbent material in place may be utilized.

Where standard-type nitrocellulose strips with a backing are utilized as the first and second membranes, in one embodiment, the membranes have different pore sizes. For example, and as discussed in more detail hereinafter, if membrane 31 (for the conjugate migration) has a 3μ pore size, and membrane 32 (for the sample migration) has a 15μ pore size, sample applied to membrane 32 will tend to migrate and stay in the sample membrane 32 and will tend not to migrate into the conjugate membrane 31.

The immunoassay of FIG. 1 may be utilized as follows. First, a sample (not shown) possibly containing antibodies (or antigens) is provided to the second opening or hole 26 and allowed to migrate through the second sorbent material 32 to its second zone 63 which is contact with the second zone 33 of the first sorbent material 30. Optionally, after providing the sample to hole 26, a measured amount of liquid such as a buffer solution may be added to hole 26 to help in the migration of the sample.

Regardless, the sample reaches the test line 50 which is printed atop the second zone 33 of the first sorbent material or infused therein. After a desired amount of time, by which time the antibodies (or antigens) in the sample (if present) will have had an opportunity to bind to the antigens (or antibodies) immobilized at the test line 50, a preferably measured amount of liquid such as a buffer solution (not shown) is added to the first opening 24. After another period of time, sufficient to permit the conjugate to migrate to the test site 50 (and control site 60 if provided), the test site 50 (and control site 60 if provided) is inspected via window 28 in order to determine whether the sample is "positive" or not. Typically, a "positive" test indicating the presence of the antibody (or antigen) in the sample is obtained when both the test site 50 and the control site 60 show lines of color. A "negative" test indicating the lack of the presence of the antibody (or antigen) in the sample is obtained when only the control site 60 shows a line of color.

The method of the invention may be expedited by providing the housing with numbering and/or lettering to indicate that hole 26 is for receiving the sample (and optionally some buffer) and is to be used first, and that hole 24 is for receiving the buffer solution and is to be used second.

Those skilled in the art will appreciate that the immunoassay 10 functions as follows. Because the test line 50 is provided with antigens (or antibodies) immobilized on a membrane, if the test sample contains antibodies to the antigens (or antigens to the antibodies), the antibodies (or antigens) will bind themselves to the antigens (or antibodies) at the test line. Thereafter, when the conjugate 39 containing an antigen for the antibody (or antibody for the antigen) coupled to a colored marker is caused to migrate to the test line, if the test sample contains the antibodies (or antigens) which are now held at the test line 50, the antigen (or antibody) of the conjugate will bind itself to the antibodies (or antigens) and the colored marker will cause a colored line to appear at the test site 50. If the test sample does not contain antibodies (or antigens), the conjugate will not have the antibodies (antigens) to bind to at the test line 50, and no colored line will appear at the test site 50. On the other hand, because the control line 60 is provided with antibodies (or antigens), the antigens (or antibodies) of the conjugate will always bind to the antibodies (or antigens) in the control line 60, thereby causing a colored line to appear at the control site 60 if the conjugate reaches the control site 60. Thus, if sufficient buffer solution is provided to the test cell, a colored line should always appear at the control site 60, thereby providing a control for the test.

Figure 2:
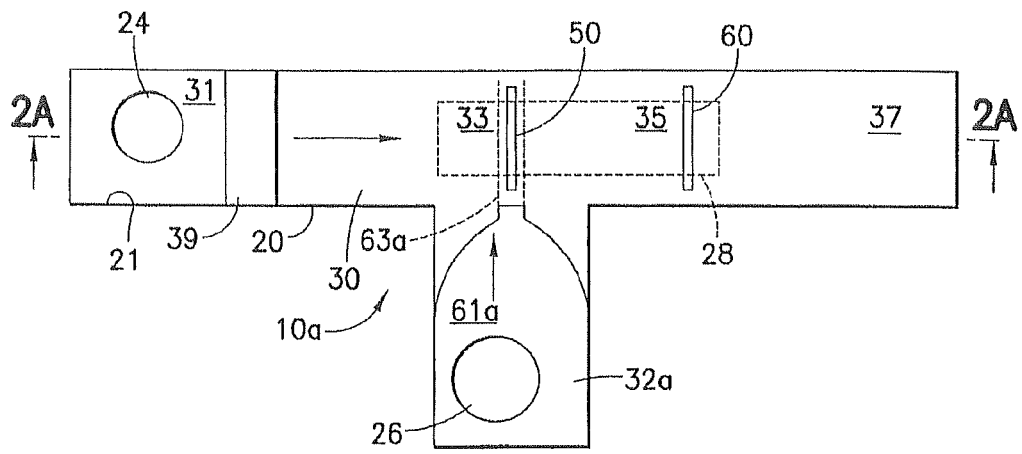
FIG. 2 is a top schematic view of a second embodiment of the invention, shown without an opener.
Figure 2A:
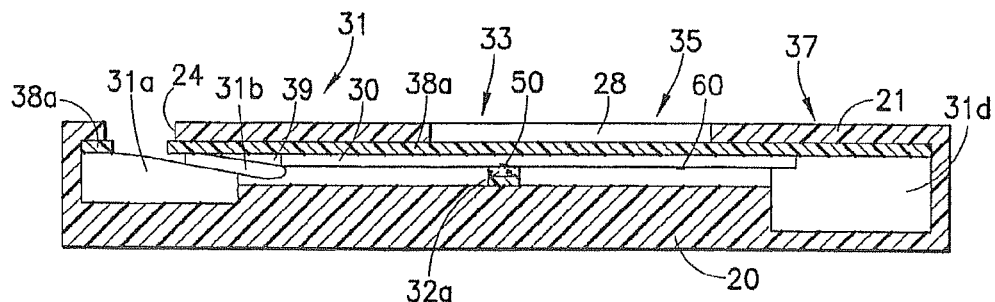
FIG. 2A is a cross-sectional view taken along line 2A-2A of FIG. 2, shown without an opener.

Turning now to FIG. 2 and FIG. 2A, a second embodiment of the invention is seen. In FIGS. 1, 1A, 1B, 2 and 2A, like numbers are used for like elements. Thus, it will be appreciated that the primary difference between the second embodiment of FIGS. 2 and 2A and the first embodiment of FIGS. 1, 1A, and 1B is that the second sorbent material 32a of test cell 10a is key-shaped (e.g., via punching). With the key-shaped arrangement, zone 61a is shaped so that it converges to the second narrow zone 63a. As a result, zone 63a touches the second zone 33 of the first sorbent material 30 almost exclusively at the location of the test line 50. Those skilled in the art will appreciate that the immunoassay test cell 10a of FIG. 2 may be used in the same manner and functions substantially the same as the test cell 10 of FIG. 1.

Figure 3:
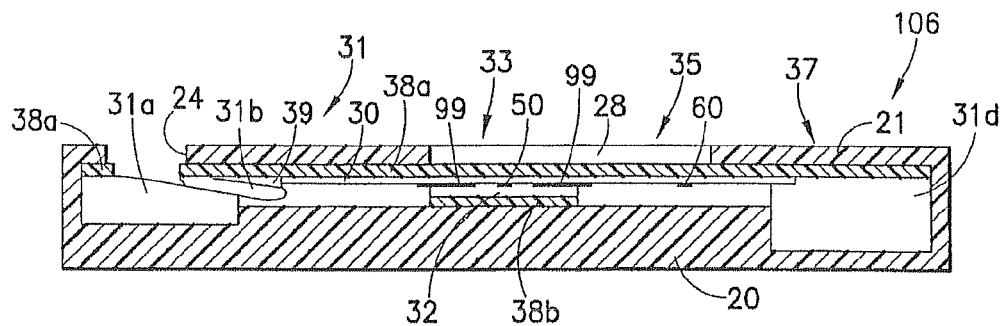
FIG. 3 is a cross-sectional view of a third embodiment of the invention, shown without an opener.

Turning now to FIG. 3, a third embodiment of the invention is seen. In FIGS. 1, 1A, 1B and 3, like numbers are used for like elements. Thus, it will be appreciated that the primary difference between test cell 10b of the third embodiment of FIG. 3 and test cell 10 of the first embodiment of FIGS. 1, 1A, and 1B is that overlying the second nitrocellulose strip 32 at the location where the first nitrocellulose strip 30 contacts the second strip (except for a narrow zone at and adjacent test site 50) is a very thin layer of non-porous material 99 such as plastic. As a result of material 99, the strips 30 and 32 contact each other almost exclusively at the location of the test line 50. Those skilled in the art will appreciate that the immunoassay test cell 10b of FIG. 3 may be used in the same manner and functions substantially the same as the test cell 10 of FIG. 1.

Figure 4:
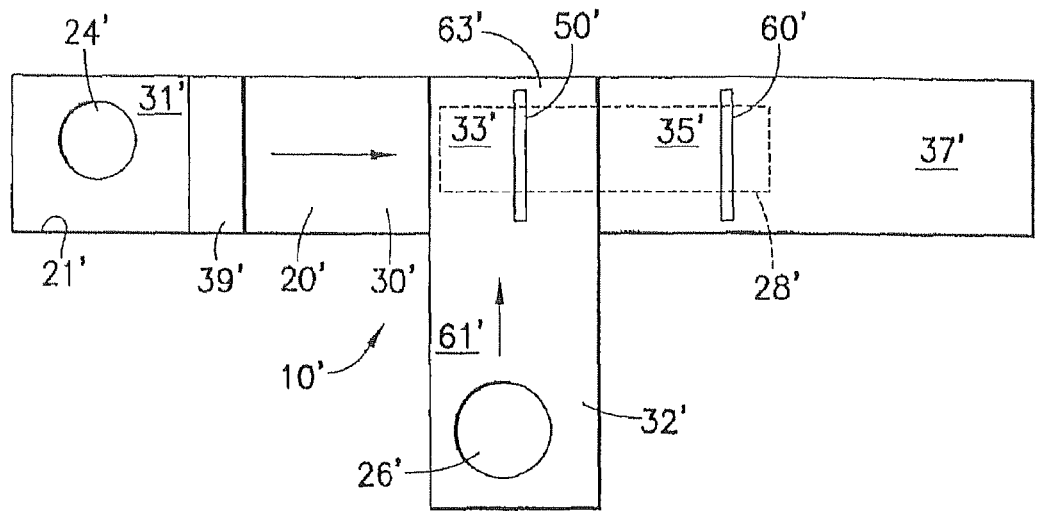
FIG. 4 is a top schematic view of a fourth embodiment of the invention, shown without an opener.

Turning now to FIG. 4, a fourth embodiment of the immunoassay device is shown with a test cell 10' (slightly modified relative to test cell 10 of FIG. 1) provided which includes: a T-shaped housing 20' having a top wall 21' defining first and second holes 24', 26', and a window 28'; and first and second sorbent or bibulous materials 30', 32' defining perpendicular horizontal flow paths in the housing. The first sorbent material 30' includes at least two and perhaps three or four zones and may be made from a plurality of materials. A first zone 31' (sometimes called a filter zone) is located at the first hole 24' and extends to a second zone 33' (sometimes called a test zone) which is located at the junction of the "T". The first zone 31' may include a filter, a pad on or in which a conjugate 39' having desired antigens or antibodies with attached colored markers is deposited and immobilized, and a thin membrane typically made from nitrocellulose (which extends to the second and optional third and fourth zones) with a backing. The first zone 31' is adapted to receive a buffer solution, to cause the buffer solution to contact the conjugate, thereby mobilizing the conjugate, and to wick the conjugate-carrying buffer solution to the second zone 33'. The second zone 33' has printed thereon a test line 50' which, as discussed hereinafter is located under the second sorbent material 32'. An optional third zone 35' (sometimes called a control zone) may be provided with a control line 60' typically containing antibodies to the conjugate antigens (or in some cases antibodies which will bind to conjugate antibodies, or even antigens which will bind to conjugate antibodies) as is well known in the art. Where the third zone 35' is provided, window 28' extends above the control line 60'. If desired, an optional fourth zone 37' (sometimes called a reservoir zone) may be provided as a wicking reservoir as is also well known in the art. The fourth zone 37' includes a relatively thicker absorbent paper. Underlying all four zones may be a thin plastic film having an adhesive which keeps the sorbent materials in place.

The second sorbent material 32' may also be made from a plurality of materials and may include two zones 61', 63'. The first zone 61' (sometimes called a filter zone) is located at the second hole 26' and extends to the second zone 63' which is in contact with the second zone 33' of the first sorbent material 30'. If desired, the second zone 63' of the second sorbent material 32' may be printed with the test line 50' having immobilized antigens or antibodies (depending on whether the test cell is designed to test for the presence of antibodies or antigens) as is well known in the art. Regardless of whether second zone 63' or second zone 33' or both are provided with the test line 50', the test line 50' may be seen through the window 28' of clear plastic provided in the housing. As is suggested by the lines in FIG. 4 (compare FIG. 1), the second sorbent material 32' overlies the first sorbent material 30', such that the thin membranes of both materials are in contact with each other at least at the test line location. The second sorbent material 32' may be shaped as in FIG. 1 so that a standard nitrocellulose strip with backing is provided. Alternatively, material 32' may be shaped as in FIG. 2 such that it touches the first sorbent material almost exclusively at the location of the test line 50'. As another alternative, the material 32' may be shaped as in FIG. 1, and a thin non-porous membrane can be provided as in FIG. 3 such that materials 30' and 32' touch each other almost exclusively at the location of the test line 50'.

Those skilled in the art will appreciate that the immunoassay test cell 10' of FIG. 4 may be used in the same manner and functions substantially the same as the test cell 10 of FIG. 1.

Figure 5:
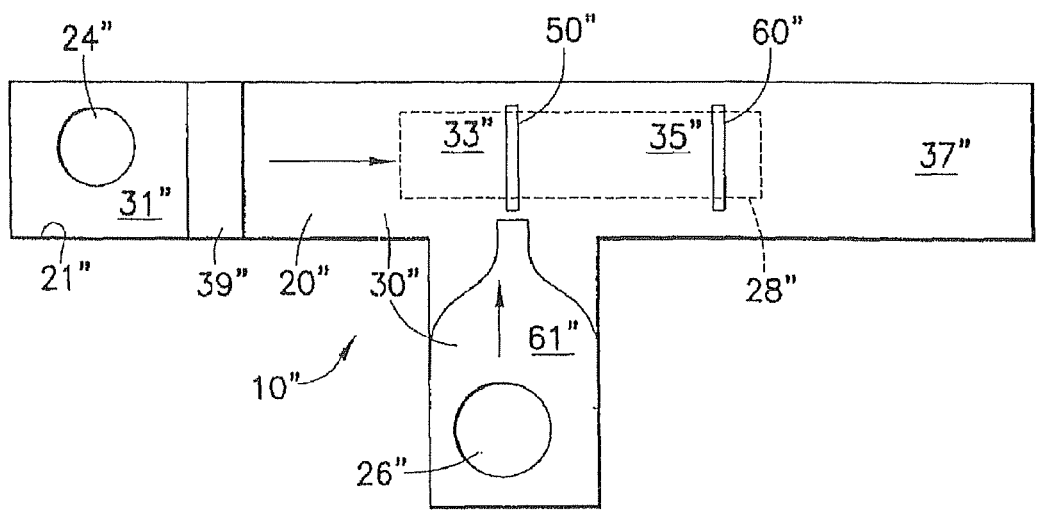
FIG. 5 is a top schematic view of a fifth embodiment of the invention, shown without an opener

Turning now to FIG. 5, an immunoassay device test cell 10" is provided and includes: a T-shaped housing 20" having a top wall 21" defining first and second holes 24", 26", and a window 28"; and a T-shaped sorbent or bibulous material 30" defining perpendicular flow paths in the housing. The T-shaped sorbent material 30" includes at least three and perhaps four or five zones and may be made from a plurality of materials. A first zone 31" (sometimes called a filter zone) is located at the first hole 24" and extends to a second zone 33" (sometimes called a test zone) which is located at the junction of the "T". The first zone 31" may include a filter, a pad on or in which a conjugate 39" having desired antigens or antibodies with attached colored markers is deposited and immobilized, and a thin membrane typically made from nitrocellulose and a backing therefor. The first zone 31" is adapted to receive a buffer solution, to cause the buffer solution to contact the conjugate, thereby mobilizing the conjugate, and to wick the conjugate-carrying buffer solution to the second zone 33". The second (test) zone 33" may be printed with a test line 50" having immobilized antigens or antibodies (depending on whether the test cell is designed to test for the presence of antibodies or antigens) on the membrane as is well known in the art. The test line 50" may be seen through the window 28" of clear plastic provided in the housing. The third zone 61" (sometimes also called a filter zone) is located at the second-hole 26", is perpendicular to the strip defined by the first and second zones, and extends to the second zone 33". An optional fourth zone 35" (sometimes called a control zone) may also be printed with a control line 60" typically containing antibodies to the conjugate antigens (or in some cases antibodies which will bind to conjugate antibodies, or even antigens which will bind to conjugate antibodies) as is well known in the art. Where the fourth zone 35" is provided, window 28" extends above the control line 60". If desired, an optional fifth zone 37" (sometimes called a reservoir zone) may be provided as a wicking reservoir as is also well known in the art. The fifth zone 37" includes a relatively thicker absorbent paper. A thin plastic film having an adhesive which keeps the sorbent materials in place may underlie all zones.

The embodiment of FIG. 5 differs from the embodiments of FIGS. 1-4 only in that instead of using two separate strips of material which overlie each other at the test zone, a single T-shaped membrane is utilized which defines a first horizontal strip with zones 31", 33" and perhaps 35" and 37", and a second (integral) strip with zone 61" which touches the first strip at test zone 33". While the embodiment of FIG. 5 does not permit the horizontal flow paths to be tailored with materials of different pore sizes, two distinct migration paths are maintained as the first and third zones are not in fluid communication with each other except via the second (test) zone.

Figure 6:
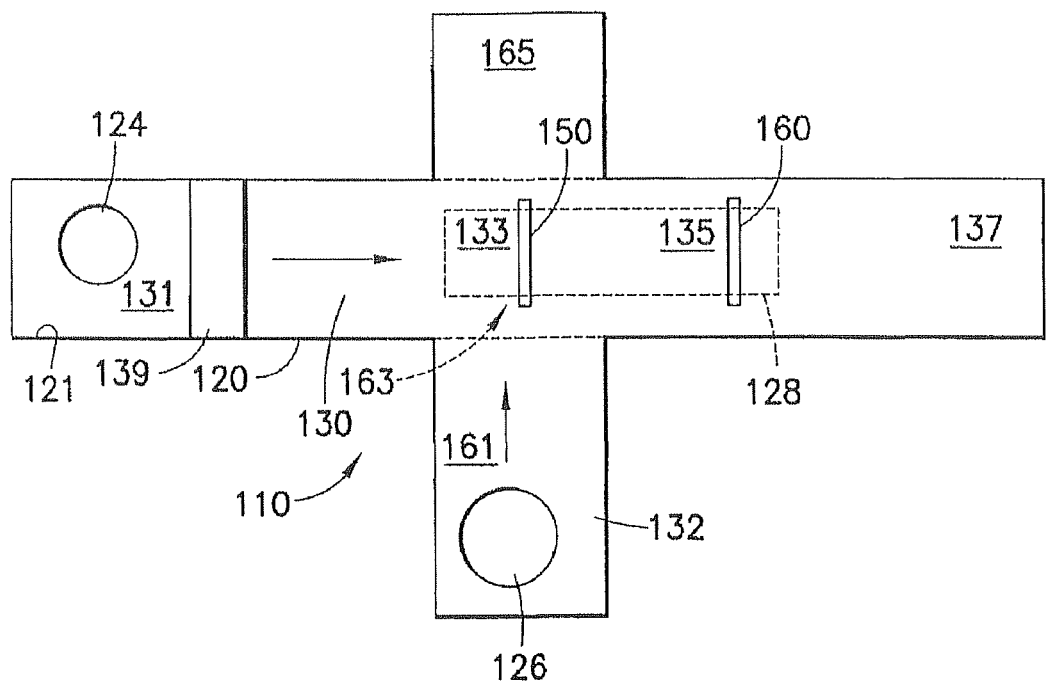
FIG. 6 is a top schematic view of a sixth embodiment of the invention, shown without an opener.

Turning now to FIG. 6, an immunoassay device test cell 110 is provided and includes: a +-shaped housing 120 having a top wall 121 defining first and second holes 124, 126, and a window 128; and first and second sorbent or bibulous materials 130, 132 defining perpendicular flow paths in the housing. The first sorbent material 130 includes at least two and perhaps three or four zones and may be made from a plurality of materials. A first zone 131 (sometimes called a filter zone) is located at the first hole 124 and extends to a second zone 133 (sometimes called a test zone) which is located at the junction of the "+". The first zone 131 may include a filter, a pad on or in which a conjugate 139 having desired antigens or antibodies with attached colored markers is deposited and immobilized, and a thin membrane typically made from nitrocellulose. The first zone 131 is adapted to receive a buffer solution, to cause the buffer solution to contact the conjugate, thereby mobilizing the conjugate, and to wick the conjugate-carrying buffer solution to the second zone 133. The second (test) zone 133 may be printed with a test line 150 having immobilized antigens or antibodies (depending on whether the test cell is designed to test for the presence of antibodies or antigens) on the membrane as is well known in the art. The test line 150 may be seen through the window 128 of clear plastic provided in the housing. An optional third zone 135 (sometimes called a control zone) may also be printed with a control line 160 typically containing antibodies to the conjugate antigens (or in some cases antibodies which will bind to conjugate antibodies, or even antigens which will bind to conjugate antibodies) as is well known in the art. Where the third zone 135 is provided, window 128 extends above the control line 160. If desired, an optional fourth zone 137 (sometimes called a reservoir zone) may be provided as a wicking reservoir as is also well known in the art. The fourth zone 137 includes a relatively thicker absorbent paper. Overlying the zones (in a manner such as seen in FIG. 1A) may be a thin plastic film having an adhesive which keeps the sorbent materials in place.

The second sorbent material 132 may also be made from a plurality of materials and may include at least three zones 161, 163, 165. The first zone 161 (sometimes called a filter zone) is located at the second hole 126 and extends to the second zone 163 which is in contact with the second zone 133 of the first sorbent material 130. If desired, the sorbent material 132 may be printed with the test line 150 at the second zone 163 instead of or in addition to second zone 133 of material 130. As is suggested by the dotted lines in FIG. 6, the first sorbent material 130 overlies the second sorbent material 132 (as in the embodiment of FIG. 1). Alternatively, the second sorbent material 132 can be made to overlie the first sorbent material 130 (as in the embodiment of FIG. 4), in which case the adhesive films where utilized, and other elements should be properly arranged. If desired, an optional third zone 165 (sometimes called a reservoir zone) may be provided as a wicking reservoir. The fourth zone 137 includes a relatively thicker absorbent paper. If desired, a thin plastic film having an adhesive which keeps the second sorbent material in place may be utilized.

Figure 7:
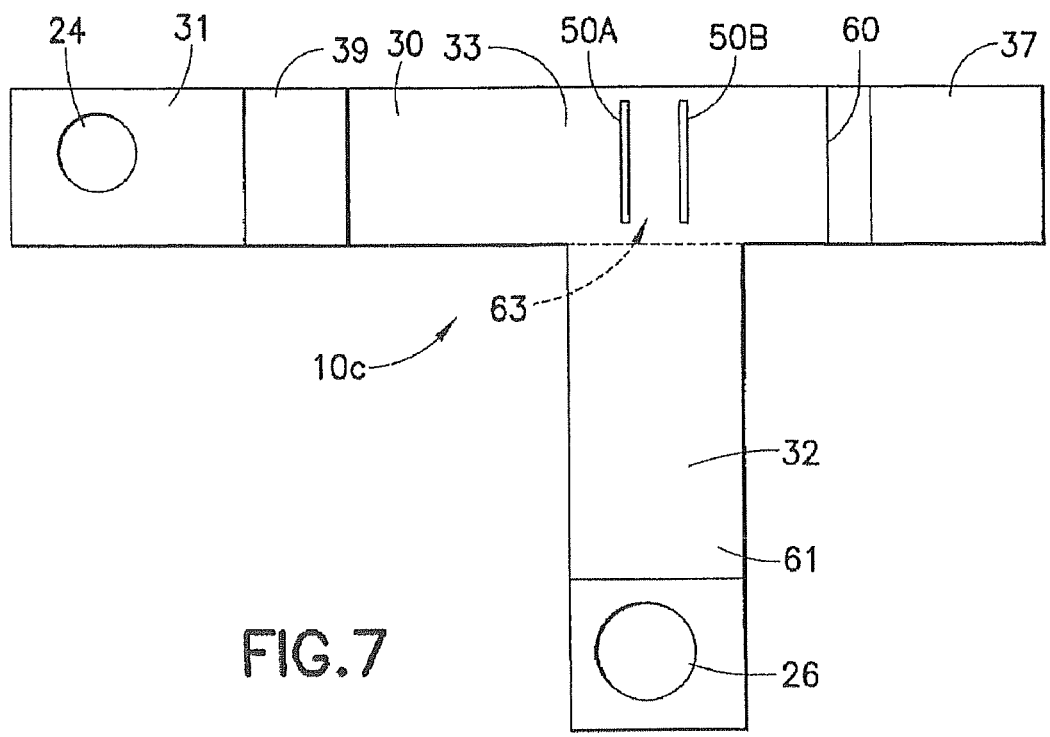
FIG. 7 is a top schematic view of a seventh embodiment of the invention, shown without an opener.

In FIG. 7, a seventh embodiment of the invention is seen. In FIGS. 1, 1A, 1B and 7, like numbers are used for like elements. Thus, it will be appreciated that the primary difference between the seventh embodiment of FIG. 7 and the first embodiment of FIGS. 1, 1A, and 1B is that two test lines 50A and SOB are printed on zone 33 of first sorbent material 30 and/or on zone 63 of second sorbent material 32. The two test lines 50A and 5OB may include different immobilized antigens or antibodies. For example, one of the lines (e.g., line 50A) could include HIV1 peptides and/or recombinant antigens such as gp41/gp120, while the other line (e.g., line 50B) could include HIV2 peptides and/or recombinant antigens such as gp36. As another example, one of the lines could include HIV1, HIV2, or HIV1/2 peptides and/or recombinant antigens, while the other line includes tuberculosis antigens. As discussed below, where the test lines include immobilized antibodies or antigens that will not bind to a single conjugate (such as Protein A), it may be desirable to use a plurality of different conjugates having desired antigens or antibodies with attached colored markers. Those skilled in the art will appreciate that the immunoassay test cell 10c of FIG. 7 may be used in the same manner and functions substantially the same as the test cell 10 of FIG. 1, except that a "positive" test indicating the presence of a first antibody (or antigen) being tested in the sample is obtained when test line 50A and the control site 60 show lines of color; a "positive" test indicating the presence of a second antibody (or antigen) being tested in the sample is obtained when test line SOB and the control site 60 show lines of color; and a "positive" test indicating the presence of both the first and second antibodies (or antigens) being tested in the sample is obtained when test lines 50A and 50B and the control site 60 show lines of color. A "negative" test indicating the lack of the presence of the antibody (or antigen) in the sample is obtained when only the control site 60 (and neither of test lines 50A and 50B) shows a line of color. An invalid test is obtained when the control site does not show a line of color.

Figure 8:
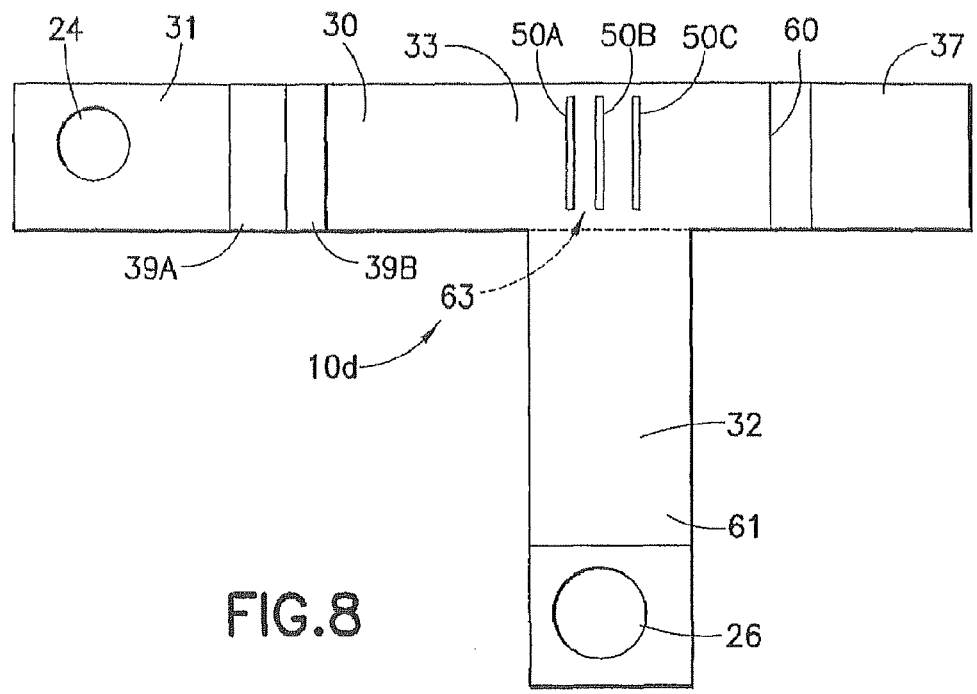
FIG. 8 is a top schematic view of an eighth embodiment of the invention, shown without an opener.

In FIG. 8, an eighth embodiment of the invention is seen. In FIGS. 1, 1A, 1B and 8, like numbers are used for like elements. Thus, it will be appreciated that the primary differences between the eighth embodiment of FIG. 8 and the first embodiment of FIGS. 1, 1A, and 1B is that three test lines 50A, 50B, 50C are printed on zone 33 of first sorbent material 30 and/or on zone 63 of second sorbent material 32, and that two different latex conjugates 39A, 39B are utilized. The three test lines 50A, 50B, and 50C may include different immobilized antigens or antibodies. For example, one of the lines (e.g., line 50A) could include p24 monoclonal antibodies, a second line (e.g., line 50B) could include HIV1 peptides and/or recombinant antigens such as gp41/gp120, while the third line (e.g., line 50C) could include HIV2 peptides and/or recombinant antigens such as gp36. In this case, two conjugates 39A, 39B are provided, with conjugate 39A being a latex conjugate with protein A which will bind to HIV1 and HIV2 antibodies, if present, but will not bind to the p24 antigen, and conjugate 39B being a latex conjugated to p24 monoclonal which will bind to the p24 antigen in the sample, if present, but will not bind to the HIV1 and HIV2 peptides and/or recombinant antigens. As shown in FIG. 8, the conjugates 39A and 39B are located at different locations of the migration path (e.g., on two portions of a single pad, or on two connected pads). However, it will be appreciated that the conjugates 39A and 39B may be applied to the same location as a mixture. Those skilled in the art will appreciate that the immunoassay test cell 10d of FIG. 8 may be used in the same manner and functions substantially the same as the test cell 10 of FIG. 1, except that a "positive" test for HIV is indicated by the visibility of color at one or more of lines 50A, 50B, 50C, and at control line 60, a "negative" test is indicated by the visibility of color at control line 60 only, and an "invalid" test is indicated when no color appears at control line 60.

Figure 9:
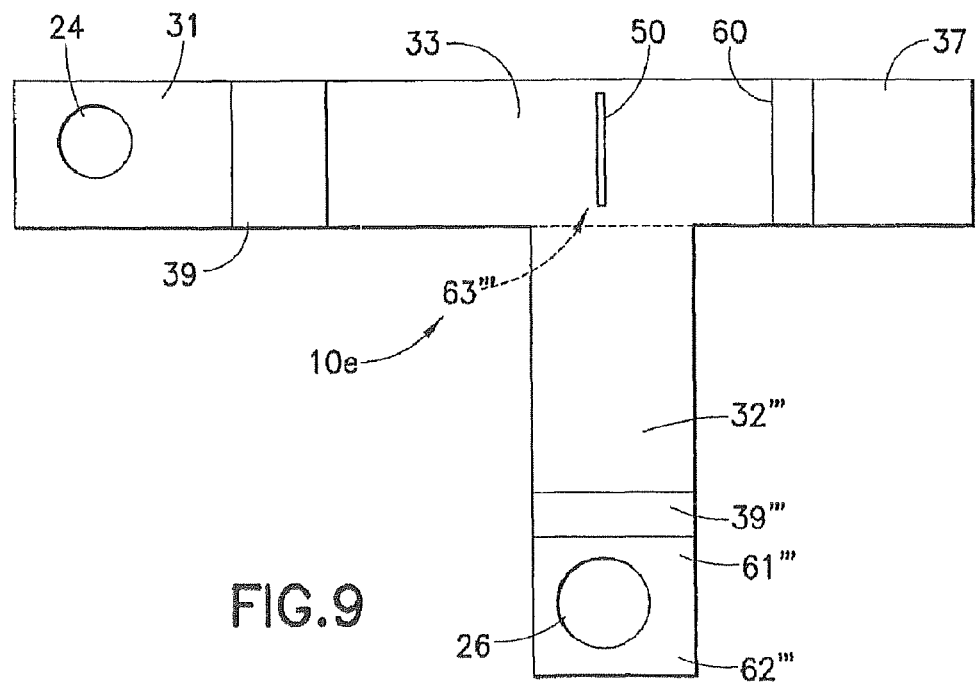
FIG. 9 is a top schematic view of a ninth embodiment of the invention, shown without an opener.

A ninth embodiment of the invention is seen in FIG. 9. In FIGS. 1, 1A, 1B and 9, like numbers are used for like elements. Thus, it will be appreciated that the primary difference between the ninth embodiment of FIG. 9 and the first embodiment of FIGS. 1, 1A, and 1B is that the second sorbent material 32''' includes a first zone 61''' (sometimes called a filter zone) having a filter or pad 62''' which has thereon a conjugate 39''' of an antibody bound to an interim binding agent (without marker), and the test zone has a test line 50 of an immobilized binding agent. The interim binding agent and immobilized binding agent are chosen for their ability to selectively bind extremely well to each other. Thus, for example, the interim binding agent may be biotin and the immobilized binding agent may be streptavidin. The conjugate 39''' in the sample migration path may therefore be an antibody such as a p24 monoclonal antibody which is bound to biotin. Likewise, the conjugate 39 in the buffer migration path may be a latex marker conjugate with an antibody (e.g., a monoclonal antibody) which will bind to the antigen of interest.

With the test cell 10 e of FIG. 9 which is arranged to detect a p24 virus, a sample is first added to the second sorbent material 32'''. When the sample reaches the p24 monoclonal antibody—biotin conjugate 39''', the p24 antigen (virus), if present in the sample, will bind with the p24 monoclonal antibody—biotin conjugate, and will migrate to the test area 63''' of strip 32''' where the biotin will be captured by the streptavidin at the test line 50 located on strip 32''' and/or on strip 30. Thus, the test line 50 will have a complex of streptavidin bound to biotin which is bound to a p24 monoclonal antibody which in turn is bound to a p24 antigen. Buffer is then added to the first sorbent material 30. The buffer carries the latex marker—monoclonal antibody conjugate 39 to the test area 33 where the monoclonal antibody of the conjugate 39 binds to the p24 antigen held at the already present complex, thereby presenting a colored line due to the marker. If no antigen is present in the sample, the biotin—p24 monoclonal antibody conjugate 39''' will still bind to the streptavidin, leaving a complex of streptavidin, biotin, and p24 monoclonal antibody at the test line. However, when the latex marker monoclonal antibody conjugate 39 reaches the test area, the monoclonal antibody will have no antigen with which to bind. Thus, no marker conjugate 39 will be held at the test line 50, and a "negative" test will be registered.

It will be appreciated by those skilled in the art that the system of FIG. 9 provides a major advantage over traditional lateral flow systems of the art due to the high affinity of the interim binding agent (e.g., biotin) and the immobilized binding agent (e.g., streptavidin) which results in an extremely sensitive test.

Figure 10:
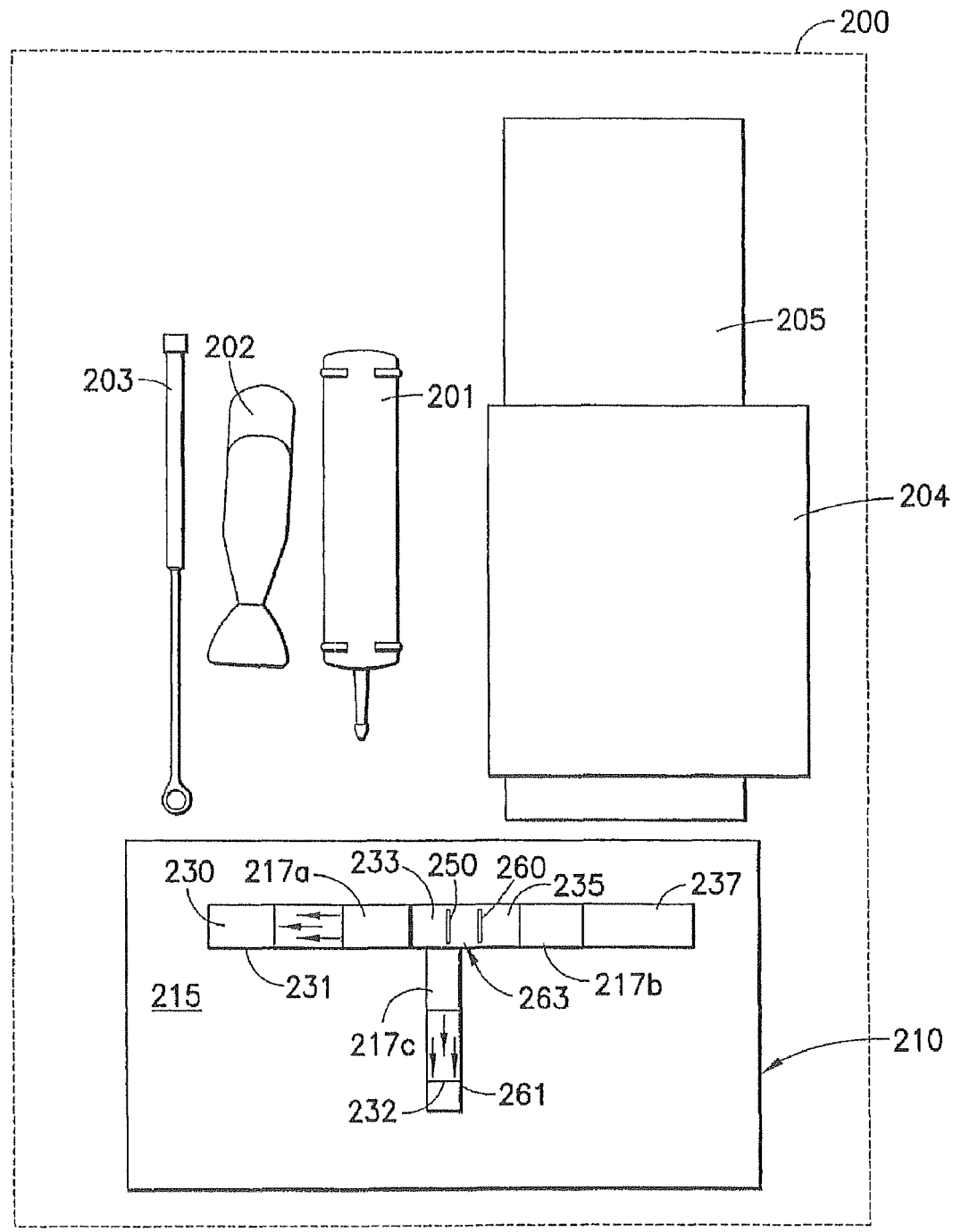
FIG. 10 is a top schematic view of an implementation of the invention which does not use a housing, and shown without an opener.

Turning now to FIG. 10, an immunoassay test kit 200 is provided and includes a lancet 201, a buffer pack 202, a loop 203, an alcohol wipe 204, an adhesive bandage 205, and a test device or test cell 210. The test cell 210 is similar to the test cells of the other embodiments, with certain exceptions such as a cardboard backing 215 which is provided instead of a housing, and paper covers 217a, 217b, 217c which are provided over various portions of the sorbent materials. Arrow indicia may be provided to indicate in which direction to pull paper covers 217a, 217b for removal from the sorbent materials. More particularly, test cell 210 includes first and second sorbent or bibulous materials 230, 232 defining perpendicular horizontal flow paths. The first sorbent material 230 includes at least two and preferably three or four zones and may be made from a plurality of materials. A first zone 231 (sometimes called a filter zone) is located at one end of the first sorbent material and extends to a second zone 233 (sometimes called a test zone) which is located at the junction of the "T". The first zone 231 may include a filter, a pad on or in which a conjugate (not shown) having desired antigens or antibodies with attached colored markers is deposited and immobilized, and a first portion of a thin membrane or sorbent or bibulous material 230 typically made from nitrocellulose with a plastic backing (not shown). The first zone 231 is adapted to receive a buffer solution, to cause the buffer solution to contact the conjugate, thereby mobilizing the conjugate, and to wick the conjugate-carrying buffer solution to the second zone 233. At least a portion of the first zone is typically covered by a paper cover 217a. The second (test) zone 233 includes a second portion of the thin membrane 230 which is may be printed with one or more test lines (one shown) 250 having immobilized antigens or antibodies (e.g., gp41/gp120 and gp36 peptides for the detection of HIV1/2) on the membrane as is well known in the art. The sorbent material at the test line 250 may be uncovered or covered by a clear plastic cover (not shown). An optional third zone 235 (sometimes called a control zone) which includes a third portion of the thin membrane 230 may also be printed with a control line 260 typically containing antibodies to the conjugate antigens (or in some cases antibodies which will bind to conjugate antibodies, or even antigens which will bind to conjugate antibodies) as is well known in the art. The third zone may likewise be left uncovered or covered by a clear plastic cover. If desired, an optional fourth zone 237 (sometimes called a reservoir zone) may be provided as a wicking reservoir as is also well known in the art. The fourth zone 237 includes a relatively thicker absorbent paper, and may be covered by cover 217b. A thin adhesive strip (not shown), which keeps the sorbent materials in place, may underlie zones 231, 235, and 237. The adhesive strip is laid down atop the cardboard 215.

The second sorbent material 232 may also be made from a plurality of materials and may include two zones 261, 263. The first zone 261 (sometimes called a filter zone) includes a filter or pad 262 and a first portion of a thin membrane or sorbent or bibulous material 232 typically made from nitrocellulose with a backing (not shown). The first zone 261 extends to the second zone 263. At least a portion of the first zone is typically covered by a paper cover 217c. The second zone 263 includes a second portion of the thin membrane 232 which is in contact with the second zone 233 of the first sorbent material 230. The second sorbent material 232 underlies the first sorbent material 230 such that the membranes are in contact with each other and such that the test line 250 is effectively located between the membranes. Thus, test line 250 could be printed on the second zone 263 of the second sorbent material 232 instead of, or in addition to the second zone 233 of the first sorbent material 230. Underlying zones 261 and 263 may be a thin adhesive strip (not shown) which keeps the second sorbent material in place. The adhesive strip is laid down atop the cardboard 215.

It will be appreciated that the test device 210 of FIG. 10 can be modified to assume any of the configurations of the previously described embodiments.

A user uses the test kit of FIG. 10 by opening a blister pack (not shown) containing all of the kit elements, removing a paper cover (if provided) from the test device 210, opening the alcohol wipe package and wiping his/her finger with the alcohol wipe 204, taking the lancet 201 and pricking his/her wiped finger in order to draw blood. Then, using the loop 203, the user may gather a drop of blood (e.g., 5 microliters) and places the drop of blood onto the non-covered portion of zone 261 of the second sorbent material 232. The user may then open the adhesive bandage package and place the adhesive bandage 205 over the pricked finger. The user then opens the buffer pack 202 and squeezes one drop (e.g., 30 microliters) of buffer onto the same location as the blood in zone 261. After waiting a desirable amount of time (e.g., 5 minutes) for the blood to migrate to the test zone 263, the user adds to two drops (e.g., 60 microliters) of buffer to the first zone 231 of the first sorbent material 230. After waiting a desirable amount of time (e.g., 7 minutes) after the buffer was added to zone 231, the test line 250 and control line 260 are viewed. A "positive" test is indicated by the appearance of color at both the test line 250 and the control line 260. A "negative" test is indicated by the appearance of color at the control line 260 and no color at the test line 250. If no color appears at the control line 260, the results of the test are invalid.

According to other embodiments of the invention, instead of providing a dry conjugate deposit having desired antigens or antibodies with attached colored markers in the test cell, the test cell does not include a dry conjugate at all. Rather, a (wet) buffer-conjugate subsystem is utilized, and the conjugate pad (31b—FIG. 1A) is not required such that the thin nitrocellulose strip or other sorbent material may be coupled directly to the filter (31a—FIG. 1A). Thus, after the sample has been deposited in the second hole in the housing and permitted to migrate to the test site, the buffer-conjugate subsystem is deposited in the first hole in the housing and likewise permitted to migrate to the test site.

According to further embodiments of the invention, instead of the viewing window being provided in the top of the housing, a window is provided in the bottom of the housing.

It will be appreciated by those skilled in the art that the embodiments of the invention may be realized using many different materials. For example, the sorbent material(s), which typically include a very thin, inert film, strip, sheet, or membrane may be formed from nitrocellulose, filter paper, silica, or from, e.g., microporous or microgranular woven or non-woven fabrics, or combinations thereof. Many types of suitable materials and combinations thereof are described in U.S. Pat. No. 4,960,691 to Gordon et al. and U.S. Pat. No. 4,956,275 to Zuk et al. which are both hereby incorporated by reference in their entireties. Often, the nitrocellulose or other sorbent materials will be provided with a thin non-porous inert plastic backing as previously described.

Thus, according to yet additional embodiments of the invention, the materials, thicknesses and lengths of the first and second sorbent materials are chosen to adjust the timing regarding the liquid sample and liquid buffer (or buffer-conjugate subsystem) reaching the test site. By providing separate migration paths for the sample/analyte and the buffer or buffer-conjugate subsystem, the materials may also be chosen to enhance sensitivity of the system.

In a similar vein, it will be appreciated that the sorbent material can be shaped in any of many manners and take any of many dimensions as is known in the art. Thus, in order to help expedite wicking, the sorbent material can be key-shaped with the strip having smaller width at the first hole which receives the buffer solution and at the test site and control site, and a wider width at a reservoir zone. Such an arrangement is shown in U.S. Pat. No. 5,989,921 to Charlton et al., which is hereby incorporated by reference in its entirety herein. In any event, generally, the test strip will be substantially greater in length than in width, and substantially greater in width than in thickness. Indeed, in at least certain embodiments of the present invention, the strip at the test zone should be paper-thin (e.g., 0.1 mm thick) and sufficiently translucent such that the test and control lines can easily be seen through the test strip.

Further, the housing and the sorbent material can be integrated in an open lateral flow platform where injection molded polymer is provided with micro-pillars which enable exact control over flow by varying the height, diameter, shape and/or distance between the pillars. Such a platform essentially uses the same material for the housing and the sorbent wicking material and is sold by Amic AB of Uppsala, Sweden. See, e.g., www.amic.se. Since the injection molded polymer may be generally transparent, the entire housing may be considered the "window" through which the test and control lines/sites may be viewed.

It will also be appreciated that depending upon the type of test being constructed (e.g., pregnancy, HIV, tuberculosis (TB), prion, urine-analysis/drug, cardiac markers, cancer markers, Chagas, Chlamydia, dental bacteria (SM/LC), influenza A, influenza B, adenovirus, rotavirus, strep A, other bacteria or viruses, etc., and even veterinary applications such as CPV, FIV, FeLV, and heartworm), the antibody (or antigen) of interest will be different, and therefore the antigen (or antibody) used in the test strip will need to be tailored accordingly. Likewise, the antigen or antibody of the conjugate will need to be tailored accordingly. In some cases (such as HIV), the identical antigen may be utilized in the test strip as in the conjugate, as the binding site of the HIV antibody will bind with the HIV antigen at the test site and still provide additional binding sites for binding to the antigen-conjugate, while in other cases, different antigens might be required. Similarly, it will be appreciated that depending upon the type of test being constructed, the control site, where provided, will need to be tailored accordingly. Thus, for example, in an HIV antibody detection test, where the ligand being identified in the test zone will be the HIV 1 and/or HIV2 antibodies, the antigen in the test zone can be a mixture of HIV1 (e.g., gp41/gp120) and HIV 2 (gp36) peptides and/or recombinant antigens. The conjugate can be a colored latex or colloidal gold conjugated to protein A, Protein A/G, anti-human IgG/IgM, peptides or recombinant antigens.

It will also be appreciated by those skilled in the art that the marker of the conjugate may take many forms including different types of metal sols, a colored latex, any of various enzymes, etc. While embodiments provide a detection signal readily visible to the unaided eye, it will be appreciated that other embodiments encompass other markers which can be detectible by ultraviolet radiation or other techniques such a fluoroscopy. Thus, it will be appreciated that a system employing the test cells of the invention which are read by an automatic reader such as a fluoroscopic or digital reader can be provided.

The present embodiments provide improved sensitivity without comprising the specificity of the assay. The main reasons for the sensitivity improvement are an improved migration of the sample to the test zone due to the distinct migration path, and the effective binding of the analyte to the binding site in the test zone prior to the reaction of the conjugated marker with the test zone complex. For example, in the case of an HIV test, HIV specific antibodies in the blood serum samples applied to the second sorbent strip will migrate to the test zone and will bind to the HIV test line(s).

No other immunoglobulin G (IgG) in the blood will bind to the HIV antigens immobilized in the test zone. When buffer solution is added to the first sorbent strip to cause the protein A conjugate with latex or gold to migrate to the test zone, the protein A conjugate will bind to the FC part of the HIV antibodies which are already captured by the HIV peptides at the test line. Because the binding between protein A and the FC part of the HIV antibodies is very strong, only a small amount of HIV antibody needs to be present in order to be detected. This is in contrast to the traditional lateral flow HIV test systems where all human IgG (including HIV antibodies) in the blood sample will bind to the protein A before migration to the test line, because protein A binds non-specifically all IgG. Thus, the entire protein A, IgG, gold/latex complex will migrate to the test line which contains the HIV antigens. Only the HIV antibodies, protein A, gold/latex conjugates will then bind to the HIV antigens. However, because of the large amount of non-related IgG in the samples and the small amount of HIV antibodies present, there is a risk that not enough HIV antibodies will bind to the protein A, and the colored line will not be visible.

The increased sensitivity of the invention was tested by comparing TB immunoassays of the invention ("New Generation") substantially as shown in FIG. 10 against standard fast test TB immunoassays (TB Stat-Pak II). Sixteen samples were generated, with two samples at each of eight different levels of antibody (32 U/ml, 8 U/ml, 2 U/ml, 1 U/ml, ½ U/ml, ¼ U/ml, ⅛ U/ml, and a control of 0 U/ml. The results of the comparison testing is seen in FIG. 11, with the immunoassays of the invention showing at least an eight-fold increase in sensitivity relative to the standard prior art tests (i.e., a positive result being detected at ¼ U/ml for the immunoassay of the invention, and a questionable result being detected at 2 U/ml for the immunoassay of the prior art). In addition, twenty test of negative samples showed no false-positive results.

The increased sensitivity of the invention was also tested by comparing HIV1 and HIV2 immunoassays of the invention ("NG HIV test") substantially as shown in FIG. 10 against standard type fast test HIV immunoassays (HIV Stat-Pak). Samples were generated with different levels of dilution (1:64, 1:128, 1:256, 1:512, 1:1024, 1:2048, 1:4096; 1:8192 for HIV-1, and 1:4, 1:8, 1:16, 1:32, 1:64, 1:128, 1:256, 1:512, 1:1024, 1:2048 for HIV-2). The results of the comparison testing is seen in FIG. 12, with the immunoassays of the invention indicating an approximately four-fold increase in sensitivity relative to the standard prior art tests (i.e., the most sensitive positive result being detected for HIV1 at the 1:4096 dilution for the immunoassay of the invention, and the most sensitive positive result being detected at a 1:1024 dilution for the immunoassay of the prior art; and the most sensitive positive result being detected for HIV2 at the 1:512 dilution for the immunoassay of the invention, and the most sensitive positive result being detected at a 1:128 dilution for the immunoassay of the prior art). In addition, one hundred twenty tests of negative samples of the NG HIV tests showed a false-positive rate of less than 1 percent.

It is believed that the immunoassay test strip devices of the invention can provide decreased assay times relative to the devices of the prior art. In particular, it is known that blood, feces or saliva will migrate very slowly in the conventional chromatographic strip tests. However, in the immunoassay assay test strip devices of the described embodiments, since a separate migration path is provided for the sample, the sorbent material utilized may be selected specifically relative to the test of interest in order to permit quick migration without concern relative to the conjugate migration, and therefore the assay time can be very fast relative to the prior art. For example, the first sorbent material 30, 30', 30", 130, 230 may be made of material having relatively small pores (by way of example and not limitation, less than 20 microns, and more preferably 3 to 15 microns), while the second sorbent material 32, 32', 32", 132, 232, may be made of material having relatively larger pores (by way of example and not limitation, more than 20 microns, and more preferably 25-40 microns). In this manner, the sample with the analyte will be able to more easily migrate down its path, while at the same time, a highly sensitive test strip line is provided on the relatively small-pored first sorbent material. In addition, as previously mentioned, by providing the second sorbent material with a pore size which is larger than the pore size of the first sorbent material, migration of the sample from the second sorbent material to the first sorbent material is desirably limited.

Examples of sorbent strips (membranes) having relatively smaller pores include MDI-08 (8 micron), MDI-10 (10 micron), MDI-15 (15 micron) from Advanced Microdevice of Ambala, India, and SP (3 micron), FP (5 micron) and RP (8 micron) from Whatman, Inc., of Floral Park, N.J. An example of a sorbent strip having relatively larger pores is P40 (30 micron) from Schleicher & Schuell Bioscience, Inc. of Keene, N.H.

Further yet, it is believed that the migration of conjugated particles in the absence of the sample provides a more uniform and consistent migration, resulting in an improvement of background clearance.

Another advantage of the immunoassay test strip devices of the embodiments is that they overcome aggregation/agglutination problems between the marker conjugate and analyte in the sample which is a major problem for large analytes (such as bacteria) in traditional chromatographic immunoassays. In the prior art, the large complex between bacteria and conjugated antibodies has difficulty in migrating to the test line. As a result, the complex tends to remain in the bottom of test strip or in the pad. With the present embodiments, the bacteria in the sample are applied (after filtering) directly to the test site, and immobilized there, while the marker conjugate is free to migrate without the sample to the test site. When the marker conjugate reaches the test site, bacteria already captured by the immobilized antibody in the test site will bind to the conjugate. Thus, the system of the present embodiments are extremely sensitive and specific.

Yet another advantage is the ability to provide tests for multiple infectious diseases with high sensitivity and without compromising specificity due to the cross-reactivity or decrease of sensitivity of multiple analytes when they have been printed as separate lines in a test zone. In particular, in traditional lateral flow assays, the sample and conjugate migrate together. If multiple test lines are provided in prior art devices, each line may retain analyte or cross-react with analyte so that the visible result at the following lines gets weaker and weaker. In contrast, with the present embodiments, samples containing several analytes will migrate to the test zone without the conjugate and will reach several lines at the same time. Thus, the analytes can bind equally to the several lines so that the same level of sensitivity can be maintained. Then, the conjugate is introduced in a distinct migration path and can bind to the complexes already immobilized at the lines. For example, for the simultaneous detection of HIV and TB antibodies in a patient sample, HIV antigens and TB antigens are immobilized as separate lines in the test zone, and the sample is provided to one strip for migration and for binding at the test zone. Buffer is then added to the other strip to permit the protein A gold or latex to migrate and bind to the HIV antigen-antibody complex and the TB antigen-antibody complex. Because of the high sensitivity of the test, TB will be detected if present. This is important, because in patients co-infected with HIV and TB, the antibody titer tends to be low for TB.

According to another aspect, where tests are provided for multiple infectious diseases (e.g., HIV and TB), different color latex particles can be used to conjugate to different antigens or antibodies provided in the conjugate pad or in the buffer solution. As a result, different color lines will appear at the test zone, with one color (e.g., red) corresponding to a first disease (e.g., HIV), and a second color (e.g., blue) corresponding to a second disease (e.g., TB).

As will be appreciated by those skilled in the art, the wait time between providing the sample to one sorbent strip, and providing buffer to the other sorbent strip can vary depending upon the viscosity of the sample and various attributes of the sorbent strip receiving the sample, including, e.g., pore size and strip length. Thus, typically, instructions will be included with the test device instructing the user to wait a predetermined amount of time (e.g., five minutes) after adding the sample (and optional buffer solution) to one strip, to add the buffer solution to the other strip. In order to obtain optimal results in the highest percentage of cases, the wait time is chosen to be substantially greater than what is actually needed. Thus, in accord with another aspect, in order to reduce wait time, visible food coloring or other water soluble dye is provided at the test site of any of the previously described embodiments. When the sample and optional buffer are provided to the test device, upon the sample migrating to the test site, the dye at the test site becomes diluted and disappears to the naked eye, thereby providing a visible indicator that the buffer may properly be added to the other strip without affecting the efficacy of the test.

With a test device provided with visible dye at the test site, the user is instructed to add the buffer solution after the color disappears at the test site. Thus, according to one method, a test device for determining the presence of a ligand in a liquid sample is provided with a test site having an immobilized ligand-binding mechanism and a visible soluble indicator. A sample is applied to the test device and the test site is viewed to observe the disappearance of the visible indicator. Thereafter, a solution (buffer) is applied to the test device. After some time, the test site may then be inspected to determine an indication of the presence or lack thereof of the ligand in the sample.

FIGS. 13A to 13G are composite photograph/instructional diagrams of an HIV 1/2 test cassette product according to the invention which utilize a visible dye at the test site. The test product is constructed substantially according to any of the previously described embodiments and is provided with a plastic cassette housing with four openings or windows. A first of the four openings is marked S+B and is provided to receive a test sample plus buffer. A second of the four openings is marked B and is provided for receiving additional buffer. A third of the four openings is marked with numbers 1, 2, 3, 4, and 5 and is provided with test lines corresponding with five different HIV antigens or peptides (preferably p24, gp41, gp120, gp160, and gp36 respectively). A fourth opening marked C is provided with the control line. Test lines appearing in the third opening are provided with a color dye (e.g., blue) so that they are visible. The control line appearing in the fourth opening is also provided with a color dye (e.g., green) so that it is visible.

Figure 13B:
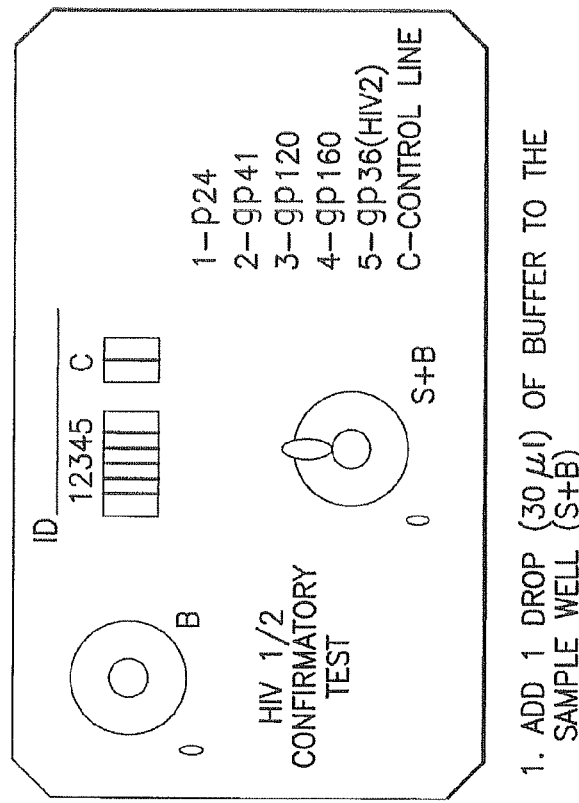
Figure 13A:
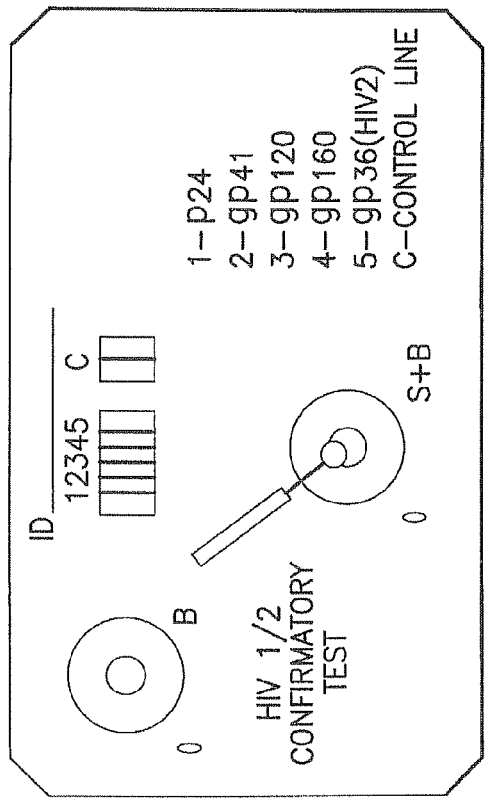
Figure 13E:
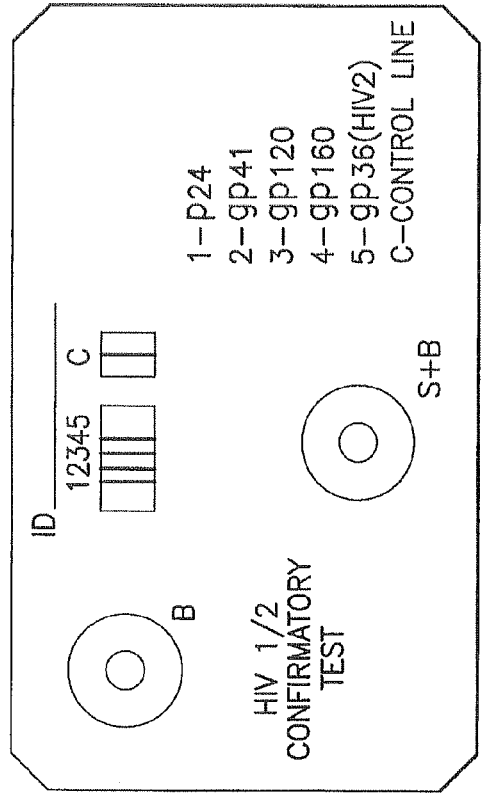
Figure 13D:
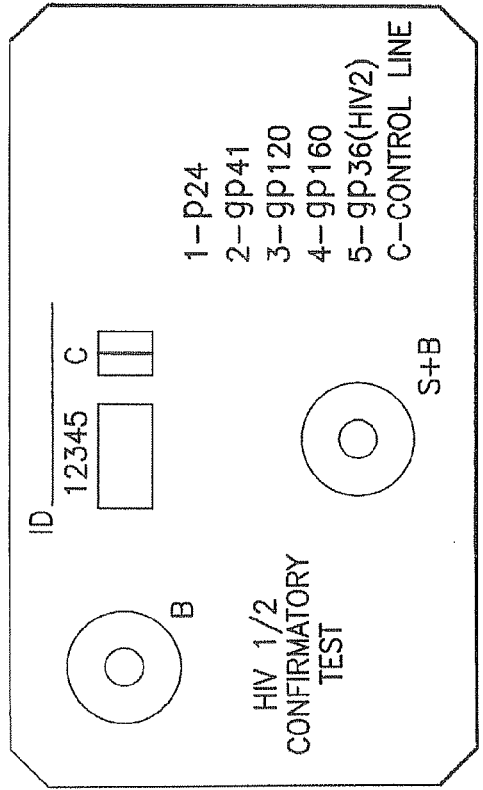
Figure 13F:
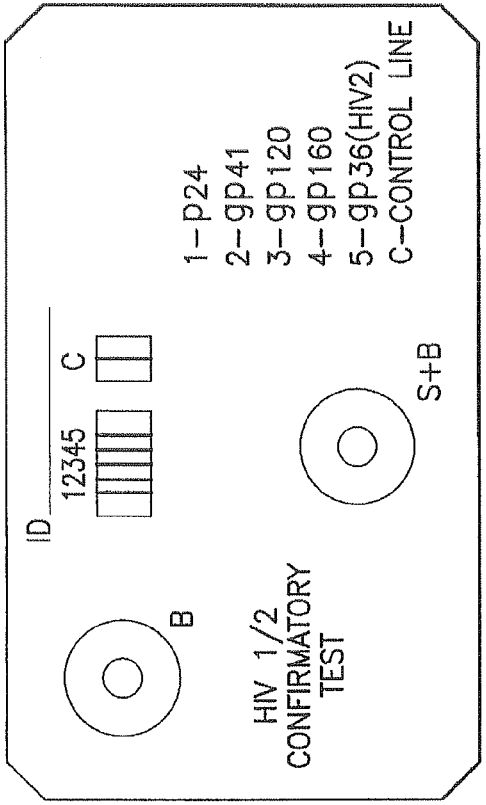
Figure 13G:
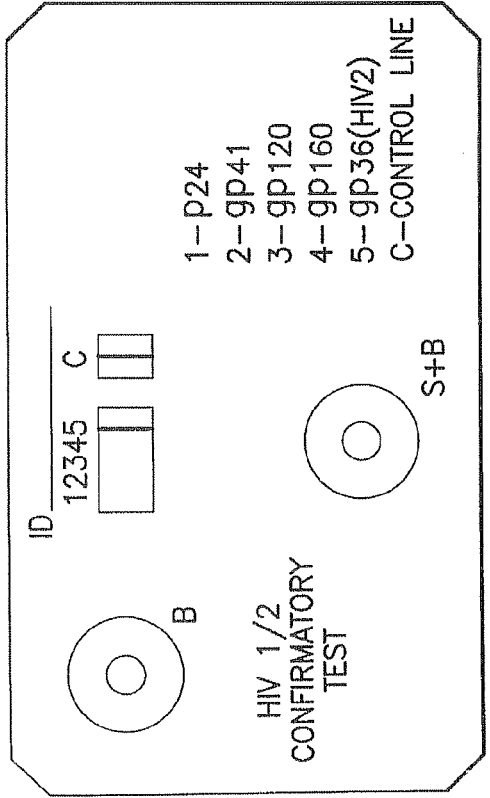

The apparatus shown in FIG. 13A is utilized by adding preferably approximately 10 μl of serum or blood to the sample well marked S+B. Then, as seen in FIG. 13B, preferably approximately 30 μl of buffer is added to the same sample well. Migration of the sample (typically with the help of the buffer) to the test zone will cause the dye at the test and control lines to dissipate. Disappearance of the dye from the lines confirms that the sample has reached the test area. At that time, and as shown in FIG. 13C, preferably approximately 90 μl of buffer is added to the opening marked B in order to cause migration of a conjugate marker to the test area. After a period of time, results may be read. Four examples of results are seen in FIGS. 13D to 13G. In FIG. 13D, only the control line C is seen, thereby indicating a valid result that the sample tested negatively for HIV1 and HIV2 antibodies. In FIG. 13E, the control line and lines 1, 2, 3, and 4 are seen, thereby indicating a valid result that the sample tested positively for four different HIV1 type antibodies but negatively for HIV2 type antibodies. In FIG. 13F, the control line and line 5 are seen, thereby indicating a valid result that the sample tested positively for HIV2 type antibodies but negatively for the four different HIV1 type antibodies. In FIG. 13G, the control line and all lines 1 to 5 are seen, thereby indicating a valid result that the sample tested positively for four different HIV1 type antibodies and for HIV2 type antibodies. It is noted that if the control line C is not seen, the test results are not interpreted as being valid.

Figure 14A:
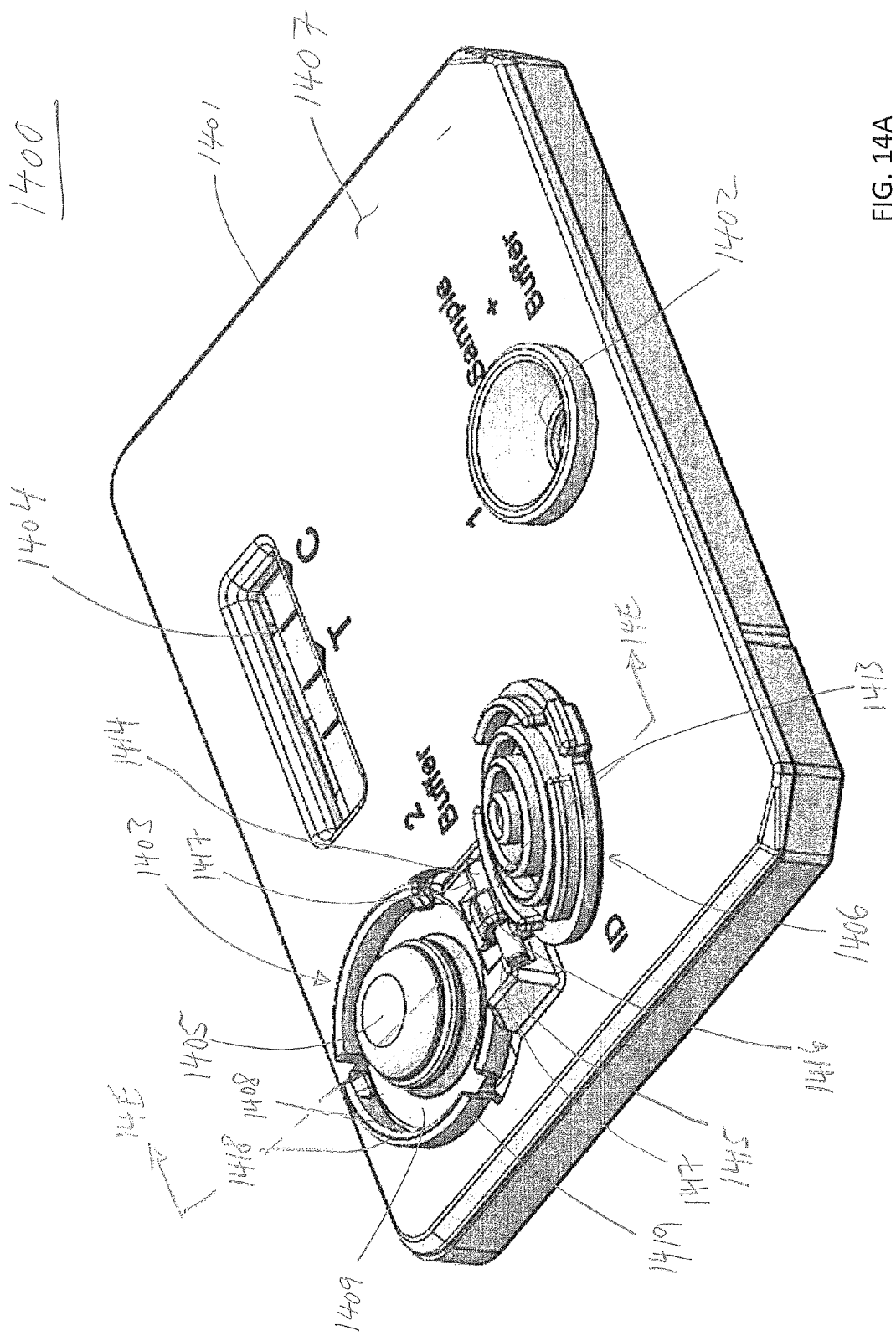
FIG. 14A is an isometric view of an embodiment of a test cassette product, shown with an opener.

FIG. 14A shows an alternative embodiment to the cassette apparatus shown in FIGS. 13A to 13G. A cassette apparatus 1400 is constructed substantially according to any of the previously described embodiments and is provided with a plastic cassette housing 1401 that defines three openings or windows. A first opening 1402 is marked "Sample+Buffer" and is provided to receive a test sample and a buffer solution. A second opening 1403 is marked "Buffer" and is provided for receiving additional buffer solution. A third opening 1404 is marked with letters "T" and "C" and is provided with test lines corresponding with at least one antigen or peptide, such as p24, gp41, gp120, gp160, and gp36 respectively, and a control line. Test lines appearing in the third opening 1404 are provided with a color dye (e.g., blue) so that they are visible. The control line appearing in the third opening 1404 is also provided with a color dye (e.g., green) so that it is visible.

One notable difference between the test cassette apparatus shown in FIGS. 13A to 13G and the test cassette apparatus 1400 is that the test cassette apparatus 1400 incorporates an integrated solution (i.e., buffer) reservoir 1405 that is coupled to the apparatus 1400 and is seated over or in the second opening 1403. For example, as shown in FIG. 14A, the reservoir 1405 is seated on a seat 1408 formed over the second opening 1403. The reservoir 1405 includes a sealed volume of a solution, such as a buffer solution. The reservoir 1405 has a housing that is formed of a breakable material, such as foil or plastic, which when pierced, permits the fluid stored therein to be squeezed or otherwise removed or drained from the reservoir 1405. In one embodiment, the reservoir 1405 is formed as a fluid filled blister.

Figure 14D:
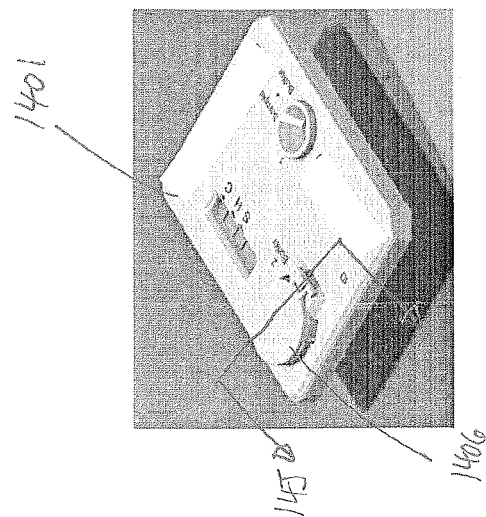
FIG. 14D illustrates the test cassette product of FIG. 14A with the opener in a fully closed position.
Figure 14C:
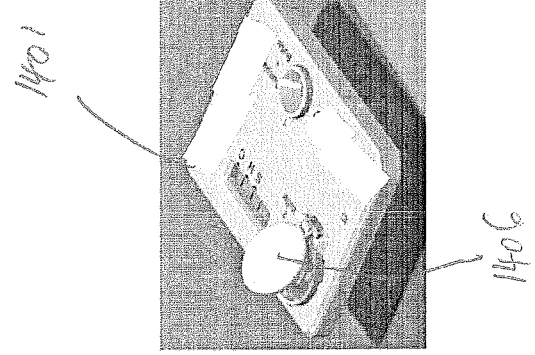
FIG. 14C illustrates the test cassette produce of FIG. 14A with the opener in an intermediate position.
Figure 14B:
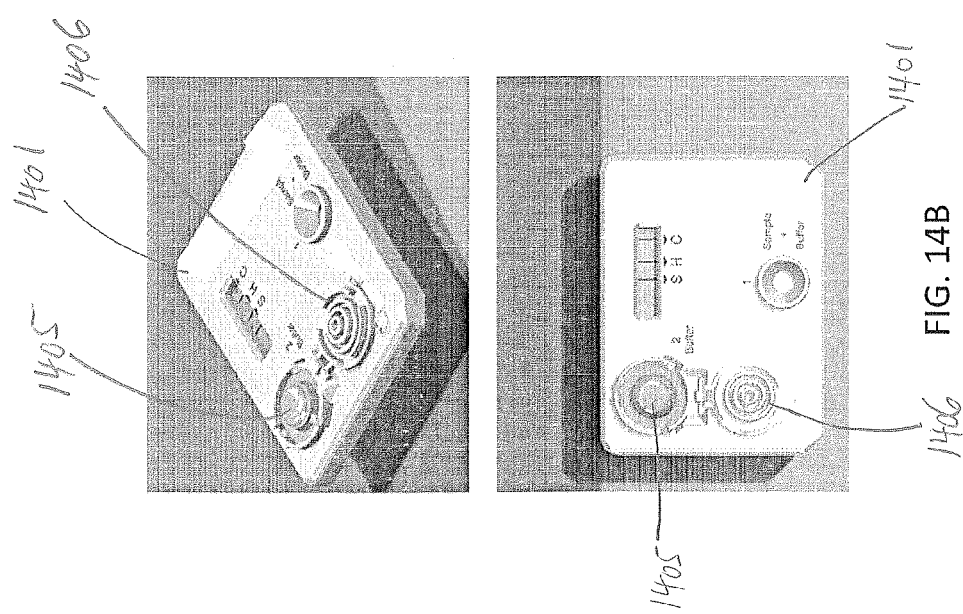
FIG. 14B illustrates the test cassette product of FIG. 14A with the opener in a fully open position.

The test cassette apparatus 1400 also includes an opener 1406 that is constructed as a press feature that may be used to apply pressure to the reservoir 1405 sufficient to cause the reservoir to rupture or otherwise open to dispense the volume of buffer solution stored in the reservoir 1405 into the housing 1401 through the second opening 1403 and onto a sorbent strip housed in the housing. The opener 1406 is constructed to rotate with respect to the housing 1401. The opener 1406 has a range of motion from a fully open position shown in FIG. 14B, through an intermediate position shown in FIG. 14C, and to a fully closed position shown in FIG. 14D. Either of the fully open or intermediate positions may be considered a first position in which the opener 1406 is not sealed or fully engaged with the housing 1401 over the second opening 1403, and the fully closed position may be considered a second position in which the opener 1406 is sealed or fully engaged with the housing 1401 over the second opening 1403. When the opener 1406 is in the first position, the opener does not open the reservoir 1405. However, when the opener 1406 is in the second position, the opener opens the reservoir 1405.

The cassette apparatus 1400 is utilized in a similar way to the apparatus shown in FIGS. 13A to 13G. First, approximately 10 μl of serum or blood may be placed in the sample well 1402 marked S+B. Then, approximately 30 μl of buffer may be added to the same sample well 1402. Alternatively, the buffer may be added to the sample outside of the test device and then the diluted sample ma be provided to the sample well. Migration of the sample (typically with the help of the buffer) to the test zone will cause the dye at the test and control lines to dissipate. Disappearance of the dye from the lines confirms that the sample has reached the test area. At that time, instead of adding buffer in droplet form from an external buffer supply as shown in FIG. 13C, a user rotates the opener 1405 from a first position (e.g., FIGS. 14B and 14C) to a second position (e.g., FIG. 14D) to effect opening of the reservoir 1405 to dispense the contents of the reservoir 1405 into the second opening 1403, which thereby causes migration of a conjugate marker to the test area. After a period of time, results may be read through the third opening 1404 in the same manner described above with regard to the test cassette apparatus shown in FIGS. 13A to 13G.

Turning again to FIG. 14A, a hinge 1415 extends from the front face 1407 of the housing 1401. The hinge 1415 is constructed to allow for a snap fit coupling with a hinge pin 1414 of the opener 1406. In FIG. 14A, the hinge 1415 includes an upper, central curved pivot 1416 and lower pivots 1417, which are spaced from one another. The upper pivot 1416 faces the lower pivots 1417 and define an axial passage therebetween in which the hinge pin 1414 may be received and retained to couple the opener 1406 to the housing 1401. More particularly, the upper and lower pivots 1416 and 1417 guide the hinge pin 1414 into snap fit engagement therebetween when the hinge pin 1414 is pushed between the upper and lower pivots 1416 and 1417. When a sufficient force is applied by the hinge pin 1414 against the upper and lower pivots 1416 and 1417, the upper and lower pivots 1416 and 1417 may deflect slightly away from each other to permit the hinge pin 1414 to be snapped fully into the axial opening of hinge 1415, thereby pivotally coupling the opener 1406 to the housing 1401. The coupling between the opener 1406 and the housing 1401 permits the opener to rotate about the hinge pin 1414 so that the opener 1406 can be rotated to the second position to open the reservoir 1405, as described above during an opening operation of the reservoir 1405.

Figure 14E:
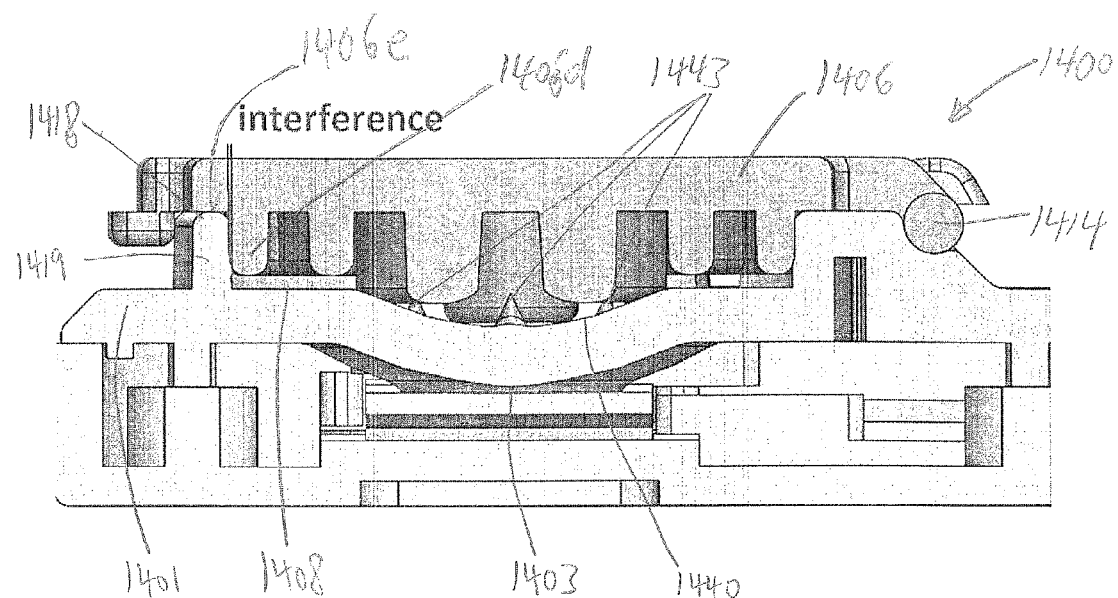
FIG. 14E is a partial section view of the cassette of FIG. 14A along section 14E-14E in FIG. 14A.
Figure 14F:
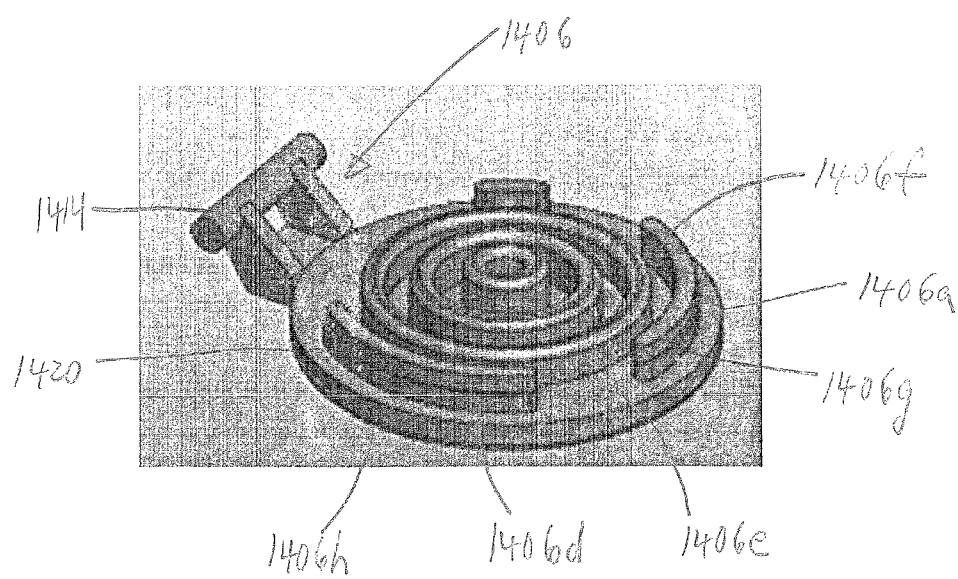
FIG. 14F is a detailed view of the opener shown in FIG. 14A.

A further description of the construction of the cassette 1400 will now be provided with reference to FIGS. 14E and 14F, where the reservoir 1405 is omitted for purposes of illustration. The seat 1408 (shown in greater detail in the assembly view in FIG. 14E) is shown as being a recessed annular seat formed in the housing 1401 around the second opening 1403. The seat 1408 is arranged to support at least a portion of the sealed reservoir 1405 (FIG. 14A). For example, as shown in FIG. 14A, the reservoir 1405 may have a generally flat peripheral flange 1409, which is in contact with the seat 1408. A surface 1440 of the housing 1401 between the seat 1408 and the opening 1403 is generally concave to direct dispensed buffer solution to drain through opening 1403. Spikes or barbs 1443 extend upwards from the concave surface 1440 around the second opening 1403. The spikes or barbs 1443 are spaced slightly from the seated reservoir 1405 such that when the reservoir is compressed during an opening procedure, the reservoir 1405 will contact one or more of the spikes or barbs 1443 which will pierce the reservoir 1405 so that further pressure on the reservoir 1405 will squeeze the solution out through the opened reservoir 1405. The fluid flowing out of the reservoir 1405 will then be directed by the concave surface 1440 into the second opening 1403 into housing 1401.

As shown most clearly in FIG. 14F, the opener 1406 may be formed generally as a disc-shaped element 1406a and a hinged connector 1406b that extends from an outer edge 1420 of the disc-shaped element 1406a. The hinge pin 1414 extends from a distal end of the hinged connector 1406b. The opener 1406 has a plurality of arcuate projections 1406d that extend from a first side 1406e of the disc-shaped element 1406a. A second side 1406h, opposite the first side 1406e, may be generally planar. The arcuate projections 1406d are radially spaced, defining arcuate channels 1406f between radially adjacent arcuate projections 1406d. When the opener 1406 is positioned in the second position, distal edges 1406g of the arcuate projections 1406d contact and apply pressure to the reservoir 1405 to open the reservoir 1405. Also, as the reservoir 1405 is being opened, the arcuate channels 1406f may direct fluid issuing from the reservoir 1405.

Turning momentarily back to FIG. 14E, when the opener 1406 is in the second position, the opener 1406 may be retained in the second position by an interference fit between the radially outermost arcuate projections 1406d and a cylindrical wall 1419 of the housing 1401 surrounding the seat 1408. In the second position the first side 1406e of member 1406a contacts a distal edge 1418 of the cylindrical wall 1419. Also, the interference fit is a fluid tight fit to prevent any leakage of fluid between the opener 1406 and the cylindrical wall 1419.

Figure 14G:
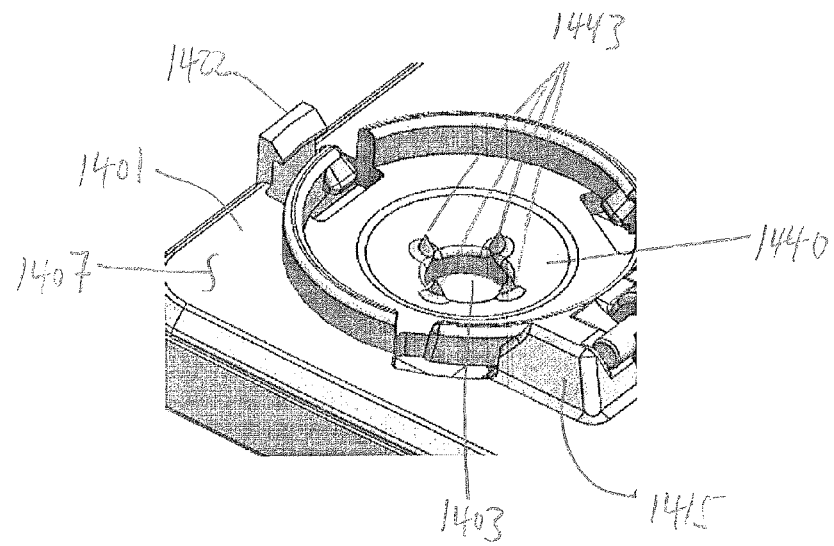
FIGS. 14G to 14I illustrate an opener similar to that shown in FIG. 14A, but modified with a locking feature.

Optionally, as shown in FIGS. 14H to 14K, the opener 1406 may include a locking feature, such as a locking tab 1406c with a tooth 1423, that engages with a mating locking feature 1422 (FIGS. 14G to 14K) of the housing 1401 when the opener 1406 is in the second position to lock the opener 1406 in the second position. In FIG. 14G, the locking feature 1422 of the housing 1401 is formed as a toothed tab that extends outwardly from the front face 1407 of the housing 1401 at a location that is diametrically opposite the hinge 1415.

Figures 14H, 14I:
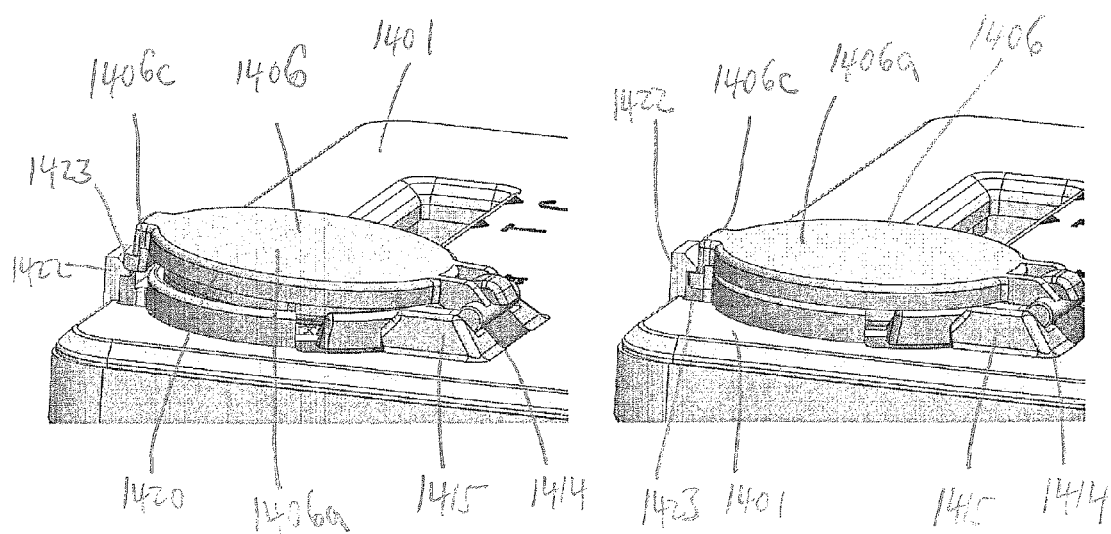

As shown in FIGS. 14H and 14I, the locking tab 1406c extends from the outer edge 1420 of the disc shaped member 1406a at a location diametrically opposite from the hinge pin 1414. The locking tab 1406c and the locking feature 1422 are constructed to engage and lock together, such as by snap fit, when the opener 1406 is moved into the second, closed position as shown in FIG. 14I.

Figure 14J:
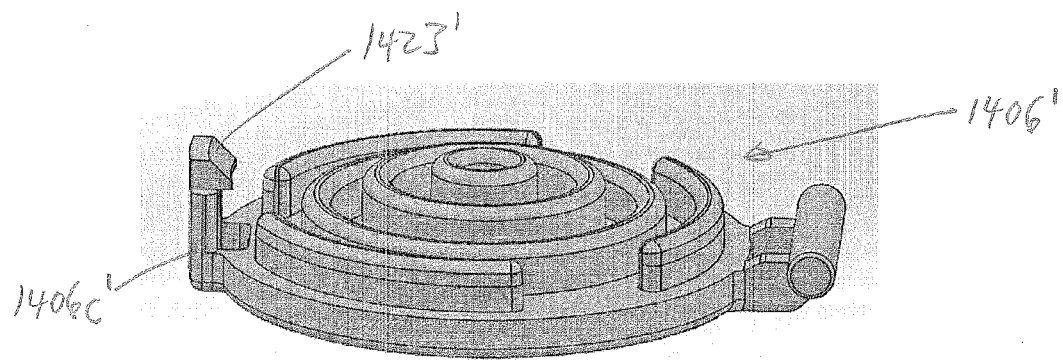
FIGS. 14J and 14K illustrate an alternative arrangement to that shown in FIGS. 14G to 14I of an opener with a locking feature.
Figure 14:
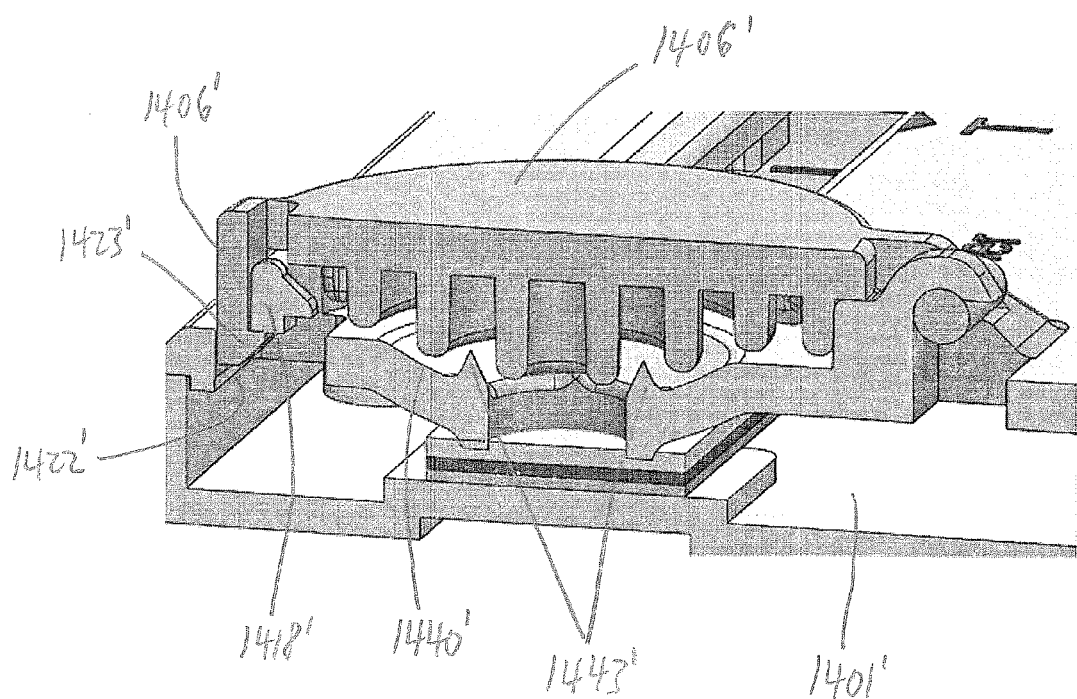
FIG. 14L illustrates an alternative placement of the hinge and opener shown in FIG. 14A with the opener shown in a first position.
FIG. 14M illustrates the cassette of FIG. 14L with the opener shown in a second position.

FIG. 14J shows an alternate opener 1406' in which the direction of locking tab 1406c' is reversed from the locking tab 1406c shown in FIGS. 14H and 14I. More particularly, as shown in FIG. 14J the tab 1406c' has a tooth 1423' that extends radially inwardly with respect to disc-shaped element 1406a', whereas the tooth 1423 of tab 1406c in FIGS. 14H and 14I is oriented generally radially outwardly with respect to disc-shaped element 1406a'.

Also, FIG. 14K shows an alternative arrangement of housing 1401' in which an opening 1422' is defined in the cylindrical wall 1418' that is constructed to receive and retain the tooth 1423', such as by snap fit connection, when the opener 1406' is moved to the second position.

Figure 14L:
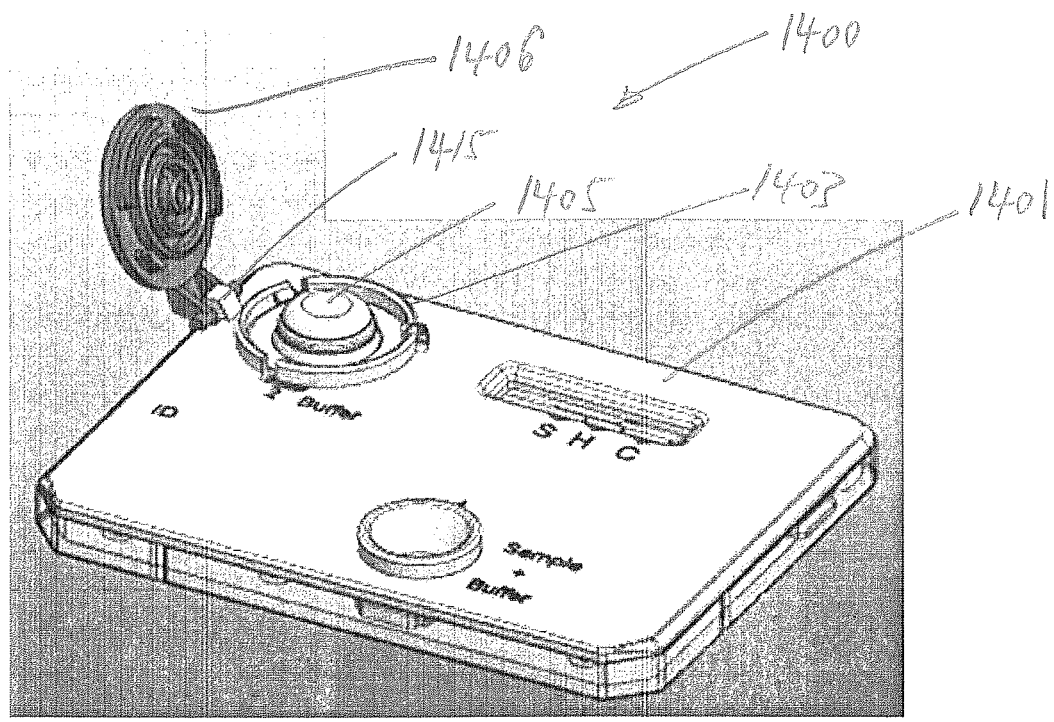
Figure 14M:
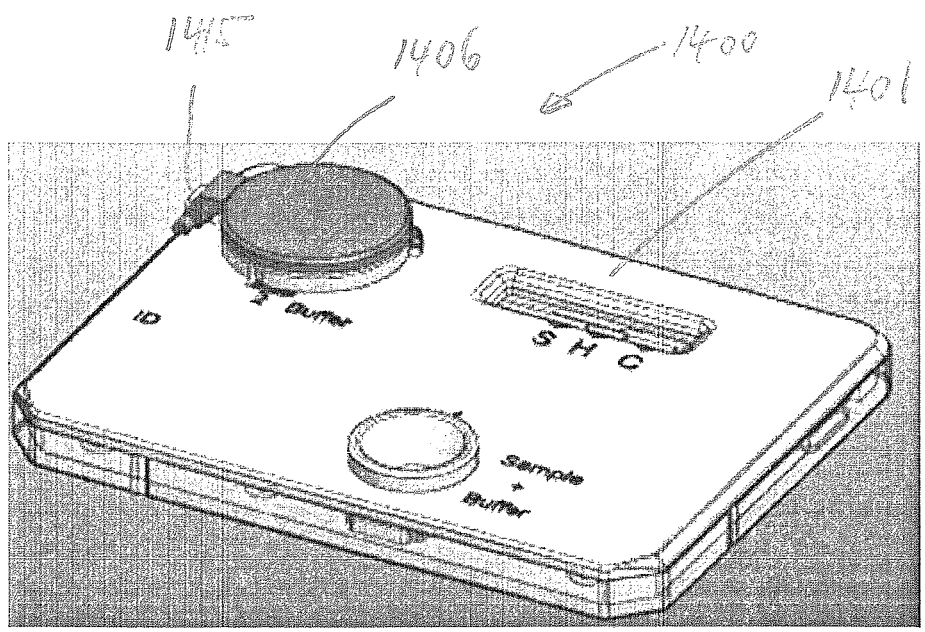

In the embodiment shown in FIG. 14A, the hinge 1415 is located at a substantially 6 o'clock position with respect to the second opening 1403. It will be appreciated, however, that the hinge 1415 may be located at different positions with respect to the second opening 1403. For example, as shown in FIGS. 14L and 14M, the hinge 1415 is shown (in FIG. 14L in a first position and in FIG. 14M in a second position) located at a 9 o'clock position with respect to the second opening 1403 (FIG. 14L).

Figure 15B:
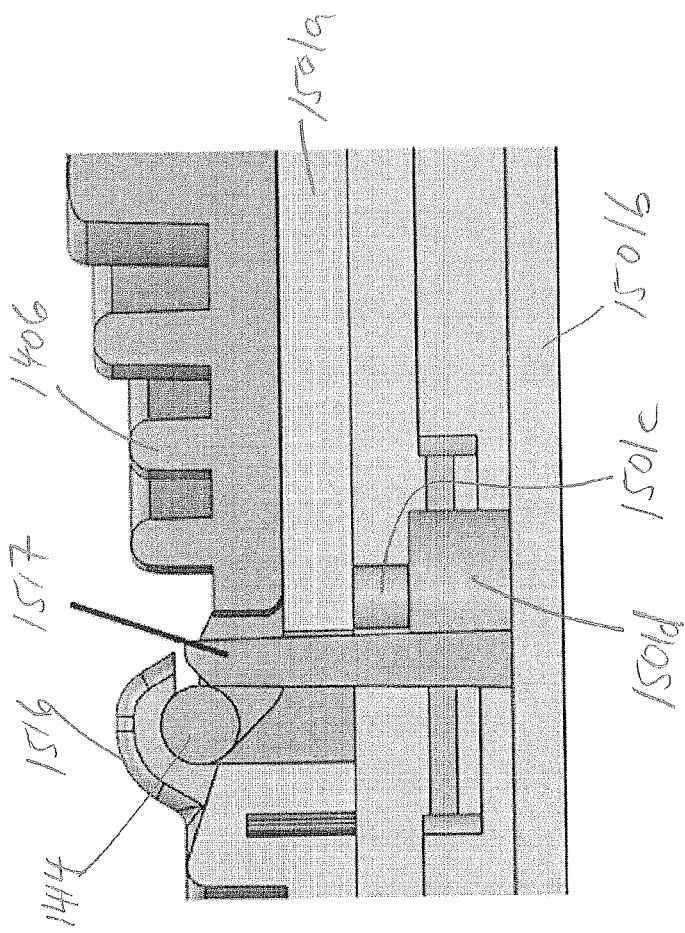
FIGS. 15A and 15B illustrate an embodiment of a test cassette apparatus that includes an interlocking hinge arrangement.
Figure 15A:
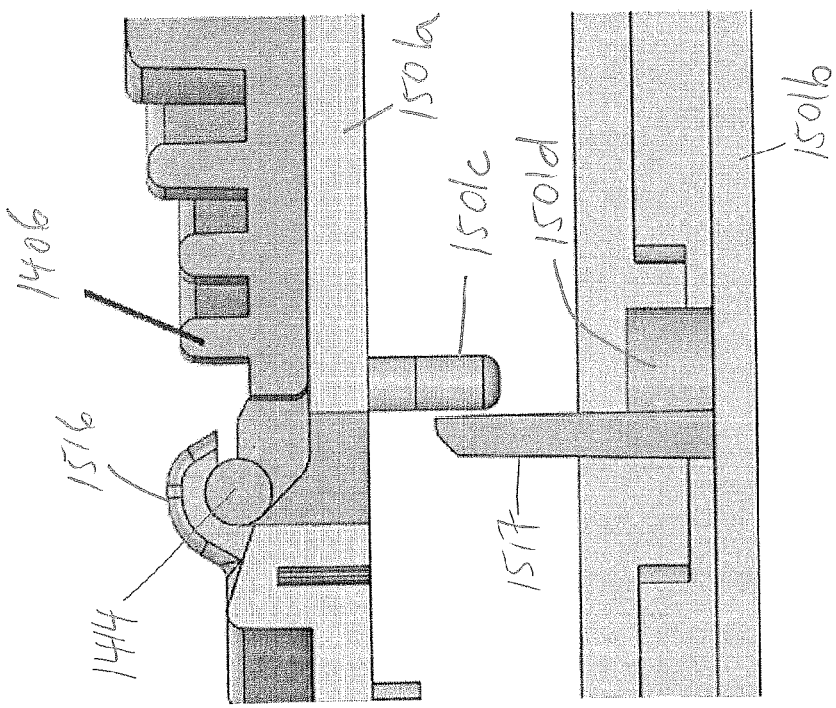

Various alternatives to the coupling arrangement between the opener 1406 and the housing 1401 shown in the embodiment of FIG. 14A are possible. In FIGS. 14A, 15A, and 15B the same numbers are used for identical elements. Otherwise, in FIGS. 15A and 15B elements corresponding to those shown in FIG. 14A are incremented by 100 with respect to elements shown in FIG. 14A.

It will be appreciated that the primary difference between the embodiment of FIGS. 15A and 15B and the embodiment of FIG. 14A is a retention element 1517 is substituted for the lower pivots 1417 of hinge 1415. FIGS. 15A and 15B show a portion of a housing 1501 that includes an upper housing 1501a and a lower housing 1501b, which are constructed to be coupled together as described below to interlock an opener 1506 between the upper and lower housings 1501a and 1501b. The retention element 1517 extends upwardly from the lower housing 1501b. An alignment member 1501c extends downwardly from the upper housing 1501a. The alignment member 1501c is constructed to align with and be received by a receptacle 1501d of the lower housing 1501b. Alignment of the member 1501c and receptacle 1501d ensures proper alignment of the upper and lower housings 1501a and 1501b when they are coupled together, as shown in FIG. 15B.

The upper housing 1501a defines an opening (not shown) through which the retention element 1517 extends when the upper and lower housings 1501a and 1501b are coupled together, as shown in FIG. 15B.

The opener 1406 may be coupled to the housing 1501 as follows. An upper pivot 1516 extends from the upper housing 1501a. When the upper and lower housings 1501a and 1501b are separated from each other, the hinge pin 1414 may be pushed against the pivot 1516, as shown in FIG. 15A. Then, the upper and lower housings 1501a and 1501b may be coupled together with the assistance of the alignment member 1501c and receptacle 1501d, as shown in FIG. 15B, so that the retention element 1517 extends through the upper housing 1501a. When the upper and lower housings 1501a and 1501b are coupled together, the retention element 1517 blocks movement of the hinge pin 1414 away from the pivot 1516, thereby pivotally coupling the opener 1406 to the housing 1500.

Figure 16A:
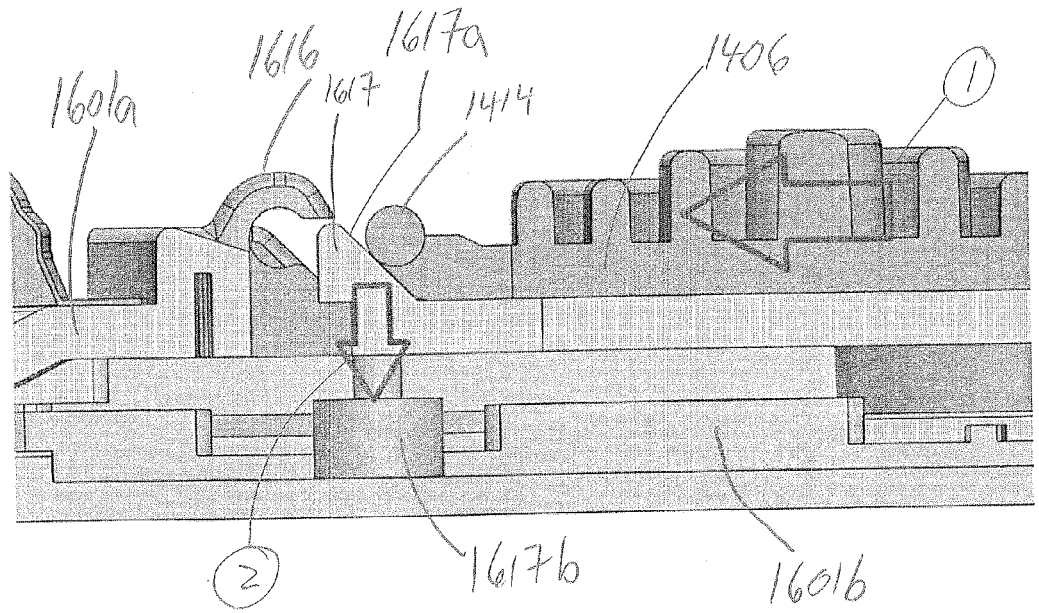
FIGS. 16A and 16B illustrate an alternate embodiment to that shown in FIGS. 15A and 15B.
Figure 16B:
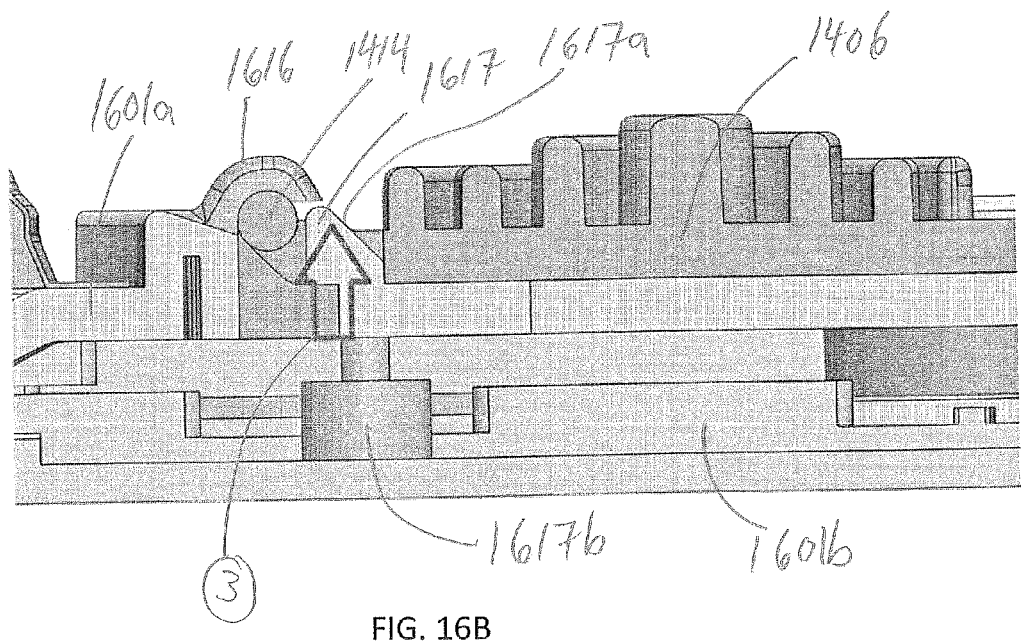

FIGS. 16A and 16B show another alternative coupling arrangement between the opener 1406 and a housing 1601. In FIGS. 14A, 16A, and 16B the same numbers are used for identical elements. Otherwise, in FIGS. 16A and 16B elements corresponding to those shown in FIG. 14A are incremented by 200 with respect to elements shown in FIG. 14A. It will be appreciated that the primary difference between the embodiment of FIGS. 16A and 16B and the embodiment of FIG. 14A is that a retention element 1617 is substituted for the lower pivots 1417 of hinge 1415. The housing 1601 has an upper housing 1601*a* and a lower housing 1601*b*, which may be coupled together. The upper housing 1601*a* may include a retention element 1617 that has a ramped surface 1617*a*. A pivot 1616 extends from the upper housing 1601*a*. The retention element 1617 is constructed to flex downward from a rest position shown in FIG. 16A when a force is applied at the ramped surface 1617*a*. Also, the retention element 1617 can flex upward toward its rest position upon removal of the applied force.

The opener 1406 may be coupled to the housing 1601 as follows. The hinge pin 1414 of the opener 1406 can be pushed laterally against the ramped surface in the direction of the arrow marked "1" in FIG. 16A, such that the retention element 1617 flexes downward in a direction of arrow marked "2" a sufficient amount so that the hinge pin 1414 can pass between the retention element 1617 and the pivot 1616. When the hinge pin 1414 passes the retention element 1617, the retention element 1617 can flex back towards its rest position in a direction of arrow marked "3" in FIG. 16B, thereby retaining the hinge pin 1414 between the retention element 1617 and the pivot 1616. Optionally, the retention element 1617 may be supported or assisted in returning toward its rest position by a biasing means 1617*b* supported by the housing 1601. For example, as shown in FIGS. 16A and 16B a spring 1617*b* may be interposed between the lower housing 1601*b* and the retention element 1617 to bias the retention element 1617 towards its rest position.

FIGS. 17A to 17C illustrate aspects of another embodiment of a cassette apparatus 1700. In FIGS. 14A, 17A to 17C the same numbers are used for identical elements. Otherwise, in FIGS. 17A to 17C elements corresponding to those shown in FIG. 14A are incremented by 300 with respect to elements shown in FIG. 14A. It will be appreciated that the primary difference between the embodiment of FIGS. 17A to 17C and the embodiment of FIG. 14A is a hinge 1715 (FIGS. 17B, 17C), which is constructed for coupling to an opener 1706 along open ends 1716 (FIG. 17B) defined by the hinge 1715, is substituted for hinge 1415. More particularly, the apparatus 1700 shown partially in FIGS. 17B and 17C includes a housing 1701 and the opener 1706, which is shown in greater detail in FIG. 17A. The hinge 1715 (FIG. 17B) extends from an upper surface 1707 of the housing 1701. The hinge 1715 extends along an axis A-A and defines axial openings 1718 at ends of the hinge 1715.

The opener 1706 has a generally disc shaped portion 1706*a* that is similar to the disc shaped portion 1406*a* of opener 1406. However, instead of the hinge pin 1414 of opener 1406, the opener 1706 has a plurality of flexible tabs 1706*b* that are spaced from an outer edge 1720 of the disc shaped portion 1706*a*. The tabs 1706*b* are constructed to be received and retained in the openings 1718 in the hinge 1715. More specifically, the tabs 1706*b* have an undeflected rest position shown in FIG. 17A.

To couple the opener 1706 to the hinge 1715 the tabs 1706*b* are spread apart from each other along axis A-A until each tab 1706*b* springs back securely into the openings 1718 in the hinge 1715. The tabs 1706*b* may not return completely to their rest position when the opener 1706 is coupled to the hinge 1715. Instead, the tabs 1706*b* may remain slightly deflected axially along axis A-A so that a residual spring biasing force remains to facilitate retention of the tabs 1706*b* to the hinge 1715. Once the opener 1706 is pivotally coupled to the hinge 1715, the opener 1706 may pivot about axis A-A to rotate towards a sealed fluid reservoir 1405 seated over an opening 1703 defined by the housing 1701, in the same manner described above with respect to cassette 1400.

FIGS. 18A to 18D illustrate aspects of another embodiment of a cassette apparatus 1800. In FIGS. 14A, 18A to 18D the same numbers are used for identical elements. Otherwise, in FIGS. 18A to 18D elements corresponding to those shown in FIG. 14A are incremented by 400 with respect to elements shown in FIG. 14A. The cassette apparatus 1800 includes a housing 1801 and an opener 1406 pivotally coupled to the housing 1801. The housing 1801 has a hinge 1815 that includes two upper pivots 1816 and a lower pivot 1817 (FIG. 18A). Also, two walls 1850 extend from the front face 1807 of the housing 1801 on outer sides of the upper pivots 1816. The upper pivots 1816 are formed as hooks that are open towards an opening 1803 (FIGS. 18A, 18B) defined by the housing 1801. The hinge pin 1414 is coupled to the hinge 1815 by inserting the hinge pin 1414 between the upper and lower pivots 1816 and 1817 in the direction of the arrow shown in FIG. 18C, which receive and retain the hinge pin 1414, such as by snap fit, as shown in FIG. 18D. The orientation of the upper pivots 1816 requires that the hinge pin 1414 of the opener be introduced in the direction of the arrow shown in FIG. 18C, which is the opposite insertion direction used to introduce hinge in 1414 to hinge 1415 in the embodiment shown in FIG. 14A. The walls 1850 support the opener 1406 and limit lateral sideways movement shown by arrows in FIG. 18B when the opener is not in the second, closed position.

Figure 19A:
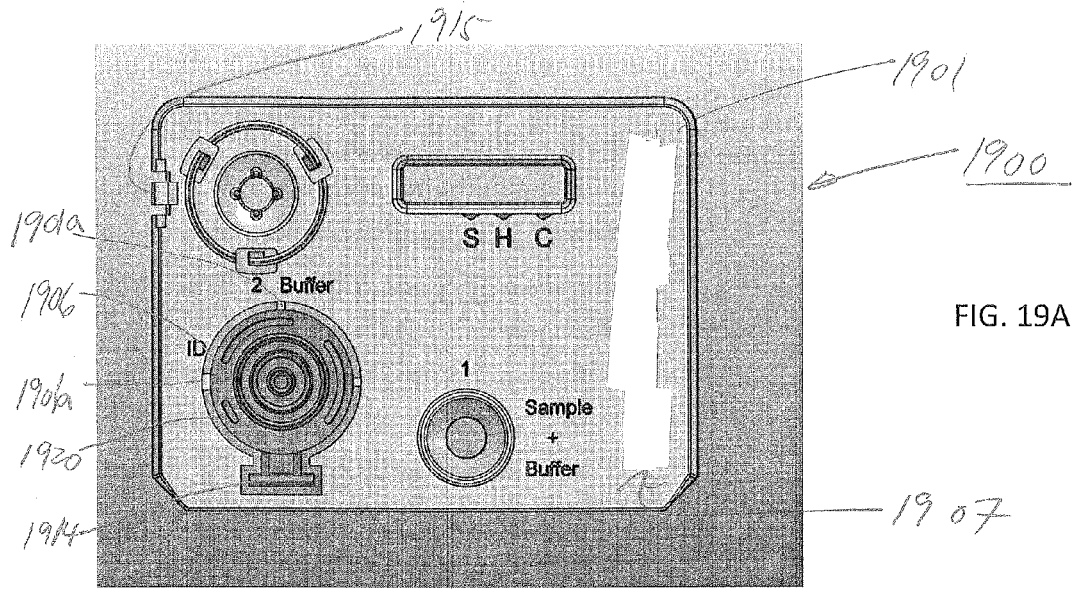
FIGS. 19A to 19C illustrate aspects of an embodiment of a test cassette apparatus that is integrally formed with a removable opener, which, when integrally formed, is disposed in an opening in a housing of the cassette.
Figure 19B:
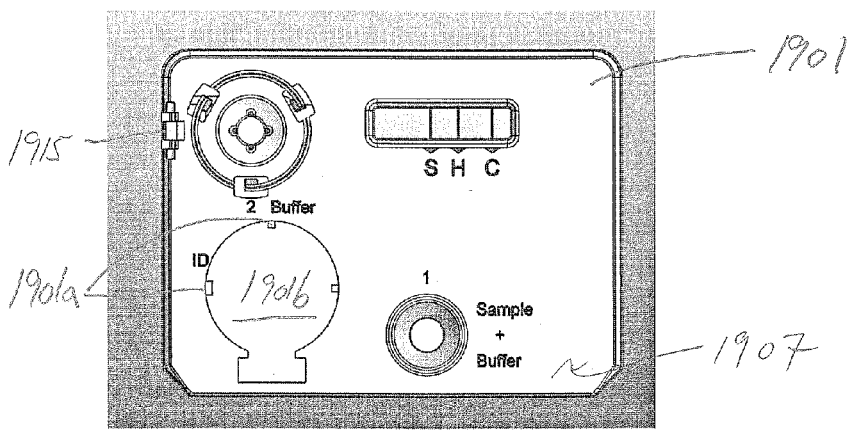
Figure 19C:
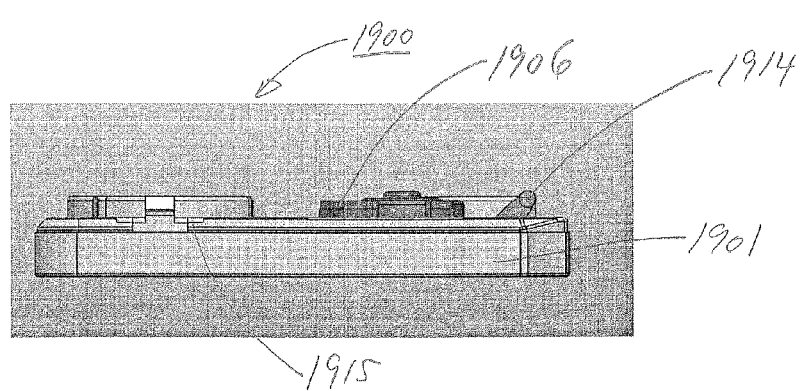

The opener 1406 may be manufactured as a separate piece from the housing or may initially be manufactured integrally as part of the housing, as shown for example in FIG. 19A. FIGS. 19A to 19C illustrate aspects of another embodiment of a cassette apparatus 1900 having similarly numbered features to the cassette 1400, except incremented by 500. The cassette 1900 has a housing 1901 and an opener 1906, which is integrally formed with the housing 1901. For example, the opener 1906 and housing 1901 may be initially molded together from the same piece of plastic. The opener 1906 may be permanently severed from the housing 1901 and then mechanically coupled to the housing 1901. Other than the integral connection to the housing 1901, the opener 1906 may otherwise have the same construction and function as the opener 1406 described above. Also, the housing 1901 may have a hinge 1915 that has the same construction and function as the hinge 1415 described above. For example, the opener 1906 includes a hinge pin 1914 corresponding to the hinge pin 1414 that may be pivotally coupled to a hinge 1915 corresponding to the hinge 1415. The opener 1906 has an outer edge 1920 that is frangibly connected to the housing 1901 at break-away portions 1901*a* of the housing 1901. The breakaway portions 1901*a* may be broken to sever the opener 1906 from the housing 1901. For example, a user may pull on or pry the hinge pin 1914 in a direction away from a front face 1907 of the housing 1901 to break the break-away portions 1901*a* and lift the opener 1906 away from the housing 1901, whereupon the opener 1906 may be coupled to the hinge 1915 in the same manner that the opener 1406 is coupled to the hinge 1415 as described above.

In the embodiment shown in FIG. 19A, the opener 1906 may be disposed in an opening 1901*b* (FIG. 19B) defined by the front face 1907 of the housing 1901 while being frangibly connected to the housing 1901. In that case, when the opener 1906 is separated from the housing 1901, the opening 1901*b* will be left visible to the user.

Figure 20A:
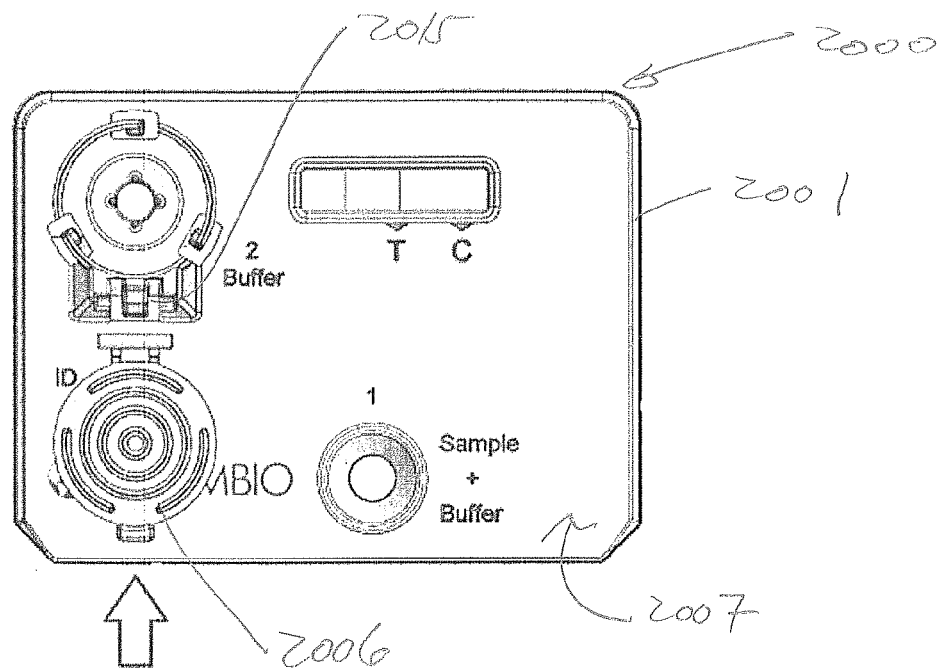
FIGS. 20A and 20B illustrate an alternative embodiment to that shown in FIGS. 19A to 19C, in which the opener is integrally formed above the surface of the housing.
Figure 20B:
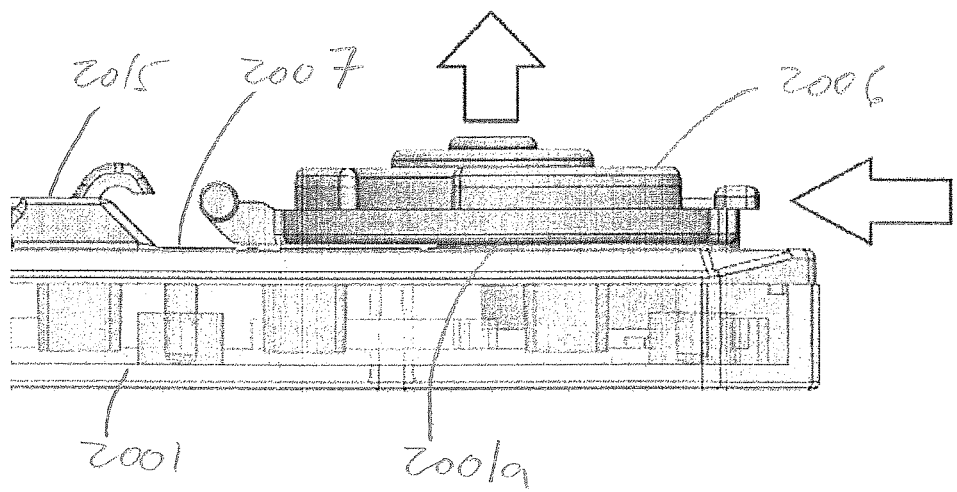
Figure 21A:
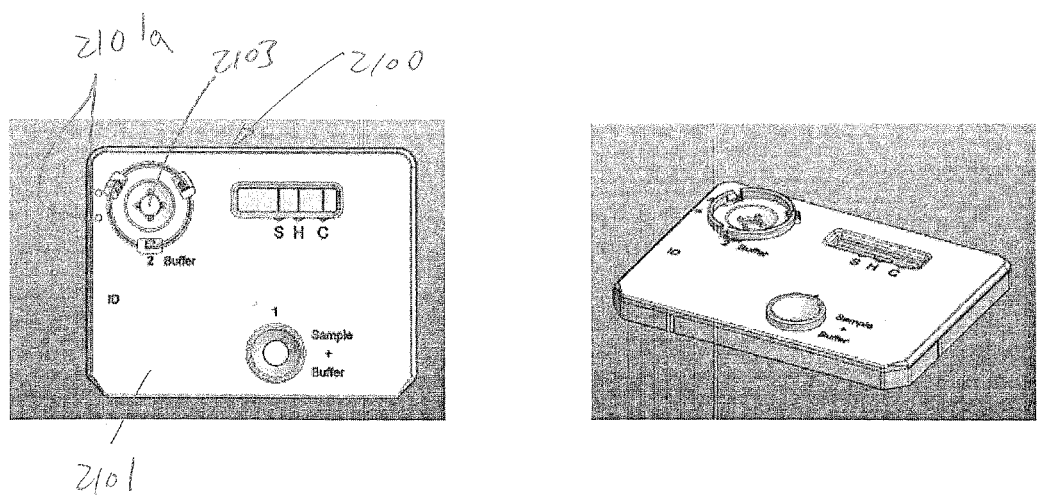
FIGS. 21A to 21D illustrate aspects of an embodiment of a test cassette apparatus that includes an opener that incorporates a living hinge that is coupled to a housing.
Figure 21B:
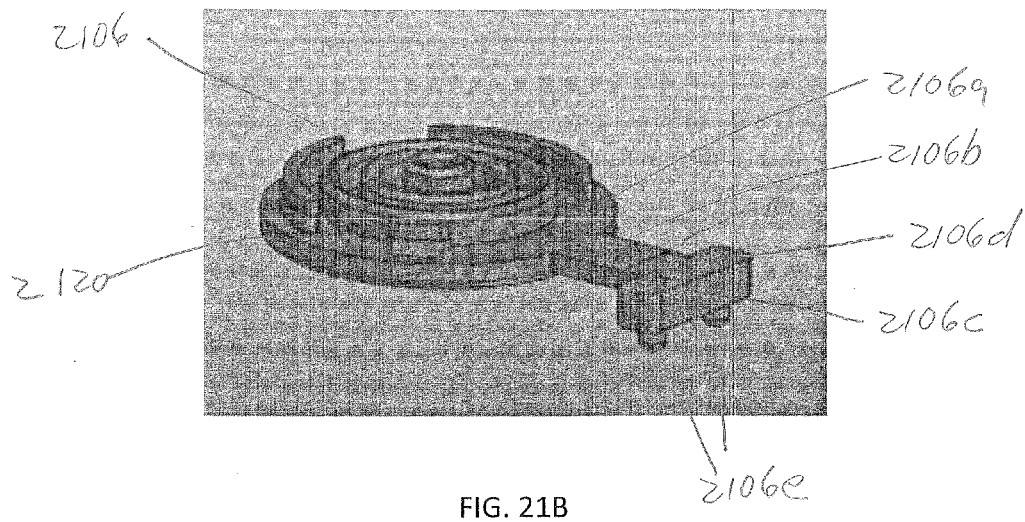
Figure 21C:
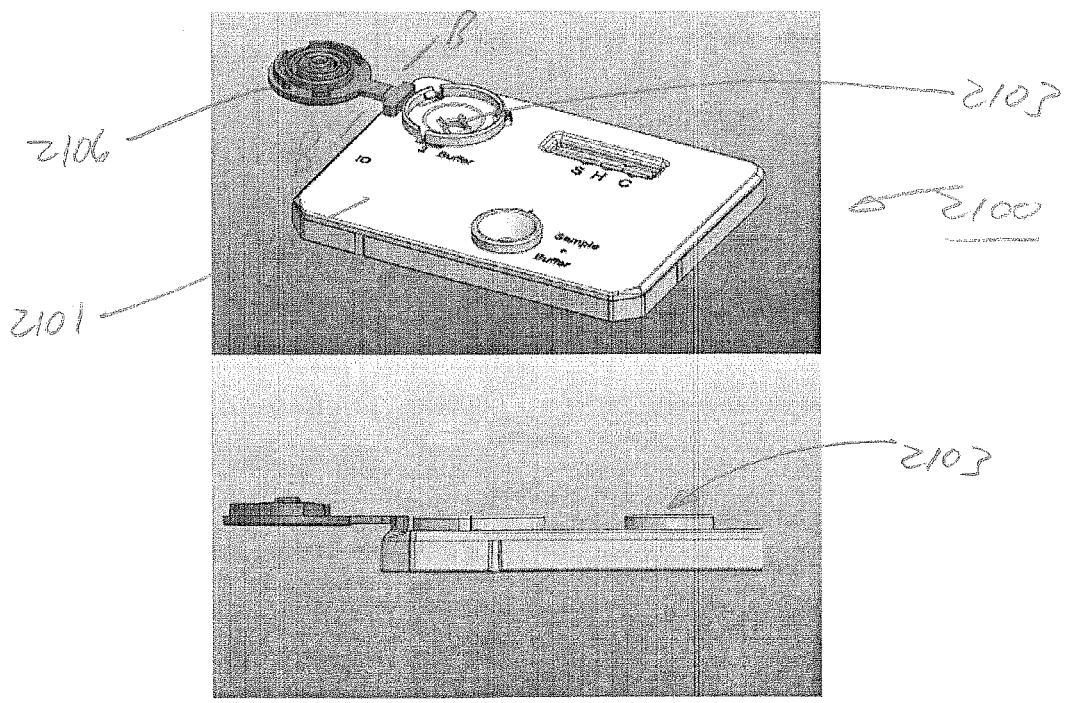
Figure 21D:
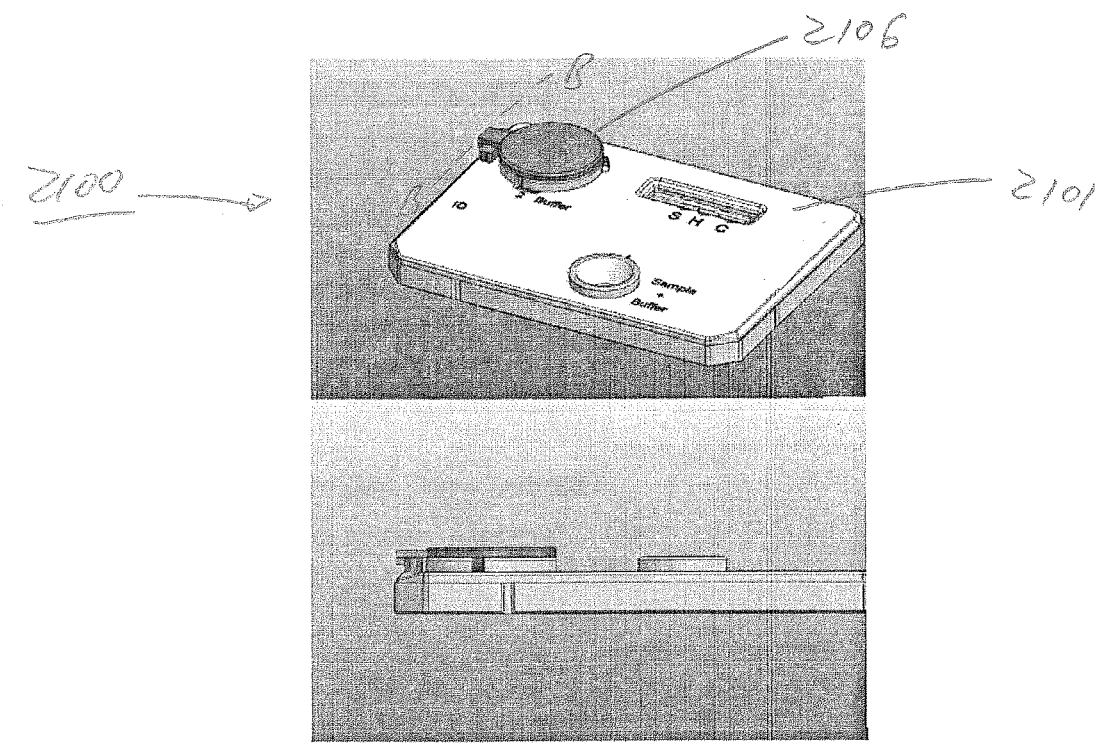

Alternatively, as shown in FIGS. 20A and 20B, an opener 2006 is disposed on, or may be slightly suspended over, a front face 2007 of a housing 2001 of a cassette apparatus 2000 that is constructed similarly to apparatus 1400 except where similar elements are numbered incrementally by 600. For example, as shown in FIG. 20B, at least some portion of the opener 2006 may be suspended (spaced) slightly away from the front face 2007 of housing 2001 by breakaway portions 2001a so that the opener 2006 projects slightly from the front face 2007 of the housing 2001, which is otherwise formed to be fully continuous and planar under the opener 2006. The opener 2006 may be severed from the housing 2001 by applying forces in the directions of the arrows shown in FIG. 20B sufficient to break the breakaway portions 2001a.

The opener 2006 may have the same construction as the opener 1406. The housing 2001 may have a hinge 2015 that extends from a front side 2007 and which may have the same construction as the hinge 1415. Thus, after the opener 2006 is separated from the housing 2001, the opener may be pivotally coupled to the hinge 2015 that extends from the housing 2001 in the same manner that the opener 1406 is coupled to the hinge 1415 as described above.

FIGS. 21A to 21D illustrate aspects of another embodiment of a cassette apparatus 2100. The cassette apparatus 2100 is shown having similarly numbered features to the cassette 1400, except incremented by 700. Among other aspects, the cassette apparatus 2100 includes a housing 2101, shown in greater detail in FIG. 21A, and an opener 2106, shown in greater detail in FIG. 21B. Unlike housing 1401, the housing 2100 does not include a hinge that extends from the housing. Instead, the housing 2101 defines openings 2101a adjacent to an opening 2103 defined by the housing 2101. The openings 2101a are configured to receive and retain tabs or projections 2106e (FIG. 21B), as described in greater detail below. Also, the opener 2106 differs from opener 1406 in that opener 2106 incorporates a living hinge 2106b that extends from an outer edge 2120 of a disc shaped element 2106a to a distal end 2106c of the hinge 2106b. A mounting bar 2106d extends form the distal end 2106c. Tabs or projections 2106e extend from the mounting bar 2106d. Thus, instead of the hinge 1415 and hinge pin 1414 arrangement of cassette 1400, the opener 2106 incorporates a living hinge 2106b which itself may be coupled to the housing 2101 by a snap fit between projections 2106e and openings 2101a.

The opener 2106 functions to open a reservoir in the same manner as described above in connection with opener 1406 of cassette apparatus 1400. In particular, the living hinge 2106b bends about axis B-B (FIGS. 21B to 21D) so that the disc-shaped element 2106a can be positioned over a reservoir (e.g., 1405) disposed over the opening 2103. Thus, as with the apparatus 1400, the opener 2106 can be positioned in a first open position shown in FIG. 21C and can be positioned in a second, closed position shown in FIG. 21D to effect opening of a reservoir disposed in the opening 2103.

FIG. 22 illustrates aspects of another embodiment of a cassette apparatus 2200 having features similar to the cassette apparatus 2100, but numbered incrementally by 100 (and incremented by 800 with respect to FIG. 14A). Notably different from apparatus 2100 is that a mounting ring 2206d shown in FIGS. 22B to 22E, which also has a retention feature to facilitate retention of the reservoir 1405 to a housing 2201 of the cassette 2200, is substituted for the mounting bar 2106d. Among other things, the cassette apparatus 2200 includes the housing 2201 and an opener 2206. The opener 2206 is shown as a generally disc shaped element 2206a. A living hinge 2206b extends from an outer edge 2220 of the disc shaped element 2206b to a distal end 2206c of the hinge 2206b, as shown in FIGS. 22B, 22C, and 22E. A mounting ring 2206d extends from the distal end 2206c. Tabs or projections 2206e (FIG. 22B) extend from the mounting ring 2206d. The tabs or projections 2206e extend from the ring 2206d and are circumferentially spaced from each other.

The housing 2201 defines openings 2201a surrounding the reservoir 1405. The openings 2201a are configured to receive and retain the tabs or projections 2206e, such as by snap fit coupling, as shown in FIG. 22C. Thus, instead of the hinge 1415 and hinge pin 1414 arrangement of cassette 1400, the opener 2206 incorporates a living hinge 2206b which itself may be coupled to the housing 2201.

As shown in FIG. 22D the ring 2206d may have an inner annular flange 2206f that may press against the peripheral edge 1419 of the reservoir 1405 when the projections 2206e are retained in the retention holes 2201a. Thus, the pressure applied by the ring 2206d may retain the reservoir 1405 to the housing 2201 over the opening 2203.

When the retaining ring 2206d is coupled to the housing 2201 as shown in FIGS. 22C to 22E, the disc shaped element 2206a can pivot about the living hinge 2206b in the direction of the arrow shown in FIG. 22E, from a first open position to a second closed position in which the opener opens the reservoir 1405, in the same manner described above in connection with opener 1406.

Figure 23:
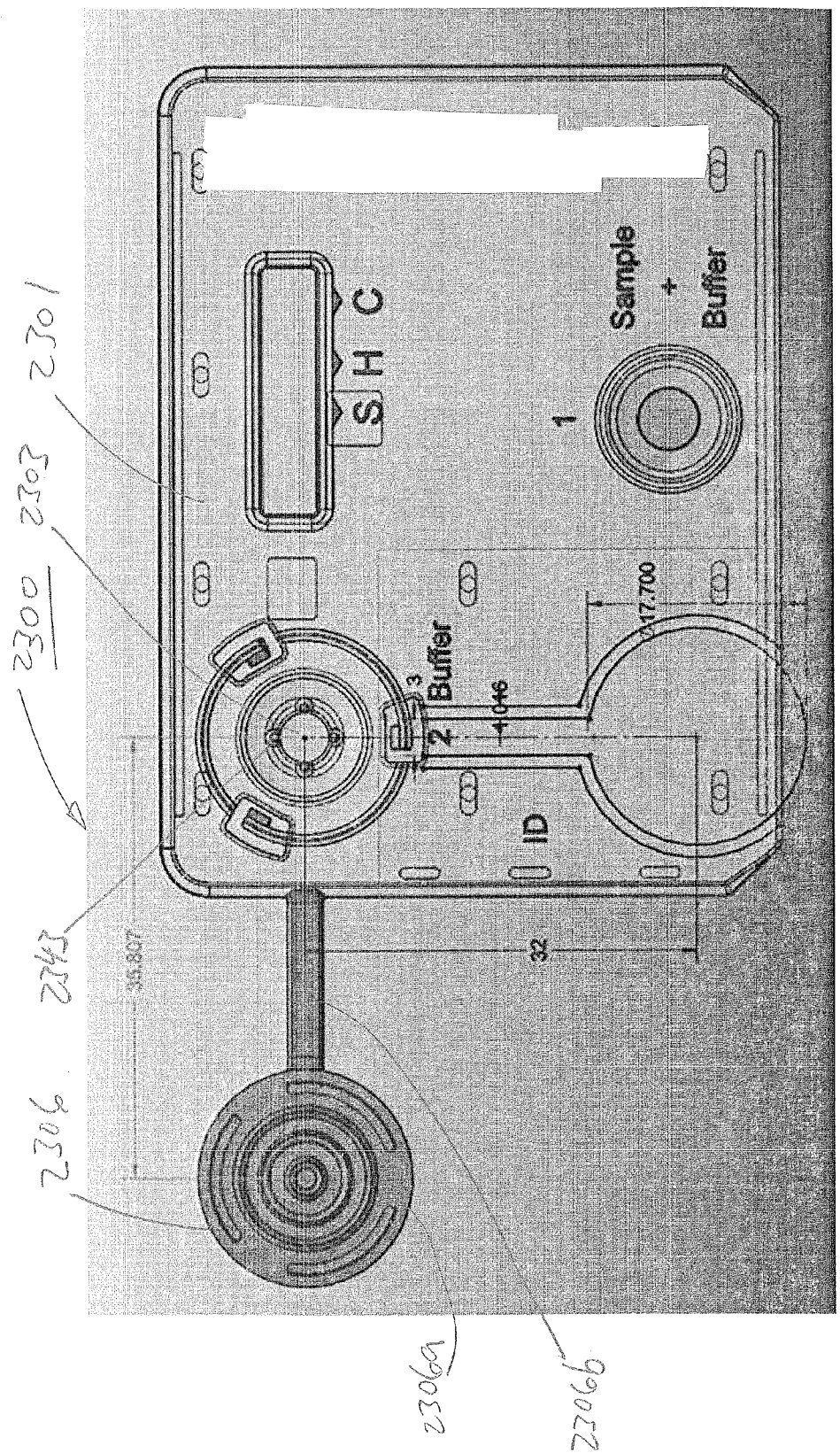
FIG. 23 illustrates aspects of another embodiment of a test cassette apparatus.

FIG. 23 illustrates another embodiment of a cassette apparatus 2300 that includes a housing 2301 and an opener 2306. The housing defines an opening 2303. The opener 2306 includes a disc shaped element 2306a and a living hinge 2306b that extends from an edge 2320 of the disc shaped element 2306a. The living hinge 2306b is integrally formed with the housing 2301 rather than being formed separately. The living hinge 2306b bends to permit the disc shaped element 2306a a range of rotational movement such that it can be moved from a first open position, shown in FIG. 23, to a second closed position in which the disc shaped element opens a reservoir 1405 coupled to the housing over opening 2303. As shown in FIG. 23, the living hinge 2306b may extend from a left side of the housing 2301 or may optionally extend from other directions. Fore example, FIG. 23 shows an alternative placement for a living hinge 230b', which extends in a direction that is 90 degrees with respect to the direction in which hinge 2306b extends.

Figure 24A:
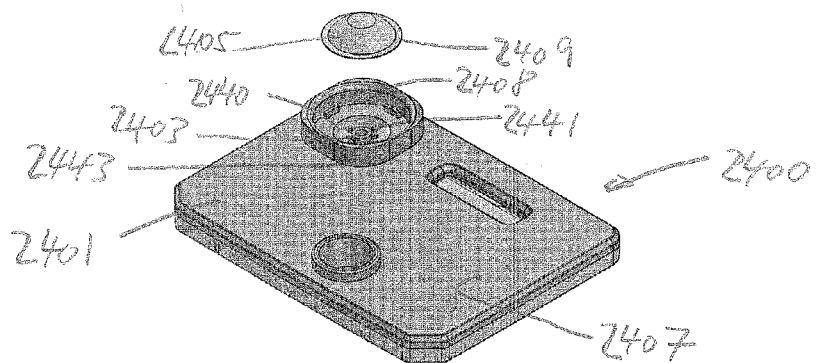
FIG. 24A shows an exploded assembly view of another embodiment of a test cassette apparatus.
Figure 24B:
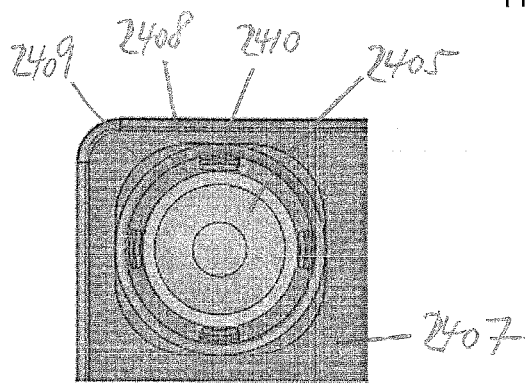
FIG. 24B shows a partial plan view of the test cassette product of FIG. 24A shown as an intermediate manufacture in which the reservoir and housing shown in FIG. 24A are not coupled.

Another embodiment of a cassette 2400 will be described with reference to FIGS. 24A to 24D. Notably, for ease of illustration, FIG. 24A is shown without an opener, such as opener 1406 or hinge 1415. It will be appreciated, however, that the cassette 2400 may incorporate any of the openers described above.

A recessed annular seat 2408 is formed in a housing 2401 around a second opening 2403. The seat 2408 is arranged to support at least a portion of the sealed reservoir 2405. The reservoir 2405 may have a generally flat peripheral flange 2409, which is in contact with the seat 2408 and may have the same construction as reservoir 1405 described above. A surface 2440 of the housing 2401 between the seat 2408 and the opening 2403 is generally concave to direct dispensed buffer solution towards drain holes 2441 defined in the surface 2440. A cylinder 2443 extends upwards from the concave surface 2440 around the second opening 2403. The cylinder 2443 is spaced slightly from the seated reservoir 2405 such that when the reservoir 2405 is compressed during an opening procedure, such as by operation of one of the openers described above, the reservoir 2405 will contact the cylinder 2443 and pierce the reservoir 2405 so that further pressure on the reservoir 2405 will squeeze the solution out through the cylinder 2443. Any fluid not flowing through the cylinder 2443 will then drain through the other drain holes 2441 into the housing.

Figure 24C:
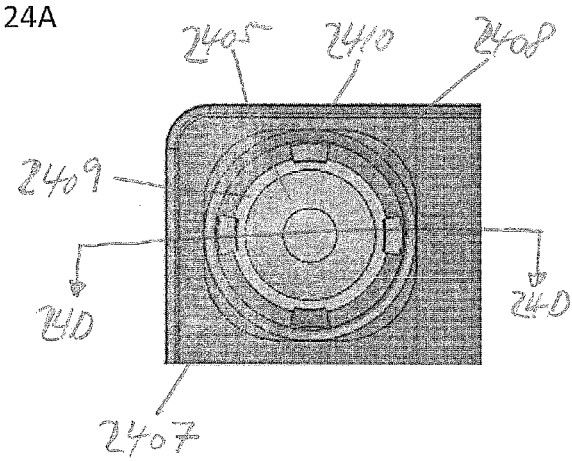
FIG. 24C shows the reservoir and housing shown in FIG. 24B coupled together.
Figure 24D:
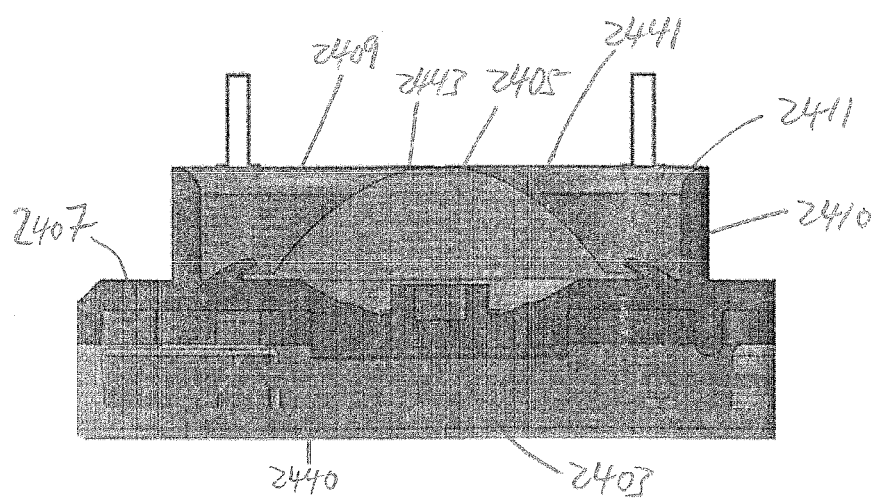
FIG. 24D shows a partial section view of the cassette of FIG. 24A along section 24D-24D in FIG. 24C during a processing step of coupling the reservoir and housing of FIG. 24A.

The reservoir 2405 may be coupled to the housing 2401 of the cassette 2400 in various ways. In the embodiment shown in FIGS. 24A to 24D, the housing 2401 may be initially formed with a plurality of heat stake tabs 2410 (shown most clearly in FIGS. 24B to 24D) that extend vertically from the seat 2408 away from the front face 2407 of the housing 2401. In the undeformed state of the tabs 2410 shown in FIG. 24B, the flange 2409 of the reservoir 2405 is disposed between the heat stake tabs 2410. During an assembly operation, for example, a heated head 2411 (FIG. 24D) presses on the tabs 2410, which deforms the tabs 2410 over the blister flange 2409, thereby coupling the reservoir 2405 to the housing 2401, as shown in FIGS. 24C and 24D.

In the various embodiments of cassette apparatuses described herein, the openers and housings may be formed of the same or different materials. The openers and housings may be formed of plastic materials, although other materials are possible. Some plastics that may be used include by way of example, high-density polyethylene (HDPE) and polypropylene (PP).

There have been described and illustrated herein several embodiments of a test cassette apparatus. While particular embodiments have been described, it is not intended that the invention be limited thereto, as it is intended that the invention be as broad in scope as the art will allow and that the specification be read likewise. Thus, while particular openers have been disclosed, it will be appreciated that other openers may be included as well. In addition, while particular types of plastic materials have been disclosed, it will be understood that other types of plastics can be used. For example, and not by way of limitation, ABS plastic and high-impact polystyrene (HIPS). Moreover, while particular configurations have been disclosed in reference to pivotal coupling arrangements between an opener and a housing it will be appreciated that other configurations could be used as well. It will therefore be appreciated by those skilled in the art that yet other modifications could be made to the provided invention without deviating from its spirit and scope as claimed.

What is claimed is:

1. A test device for use with a liquid solution the test device comprising:
   a) a housing that houses a plurality of sorbent strips, at least one strip having a location for receiving the solution, said housing defining at least an opening aligned above said location for receiving the solution;
   b) a sealed reservoir filled with the liquid solution, said reservoir being disposed in alignment with said opening and coupled to said housing; and
   c) an opener coupled to said housing, said opener arranged to rotate from a first position, in which said opener is not in contact with said sealed reservoir, to a second position, in which said opener causes said sealed reservoir to effect a release of the solution from said reservoir and into said opening and onto said sorbent strip housed within said housing.

2. The test device according to claim 1, wherein:
said opener is pivotally coupled to said housing.

3. The test device according to claim 2, wherein:
said housing includes a hinge and said opener is coupled to said hinge.

4. The test device according to claim 2, wherein:
a living hinge extends from said opener to said housing.

5. The test device according to claim 4, wherein:
said living hinge is integrally formed with said opener and said housing.

6. The test device according to claim 4, wherein:
said living hinge is formed as a separate piece from said housing and is coupled to said housing by a coupler.

7. The test device according to claim 6, wherein:
said coupler includes a mounting ring connected to said living hinge, said mounting ring configured to surround said opening in said housing and couple to said housing by snap fit closure.

8. The test device according to claim 7, wherein:
said mounting ring defines an annular flange that engages an annular flange of said reservoir and retains said annular flange of said reservoir between said mounting ring and said housing.

9. The test device according to claim 1, wherein:
said opener includes a locking feature that is constructed to lock said opener in said second position.

10. The test device according to claim 9, wherein:
said housing includes a locking feature that is constructed to engage said locking feature of said opener to lock said opener in said second position.

11. The test device according to claim 1, wherein:
said opener is formed as a generally disc shaped member and has a plurality of radially spaced arcuate members extending from a first side of said disc shaped member.

12. The test device according to claim 11, wherein:
the housing includes a cylindrical wall surrounding the opening that engages at least one of the arcuate members when the opener is in the second position.

13. The test device according to claim 12, wherein:
an interference fit is formed between said cylindrical wall and a radially outermost arcuate member.

14. The test device according to claim 1, wherein:
said housing defines a generally annular seat surrounding said opening for seating said reservoir over said opening.

15. The test device according to claim 14, wherein:
said housing includes a plurality of tabs radially extending from around said seat, said tabs disposing a flange of said reservoir between said tabs and said seat.

16. The test device according to claim 1, wherein:
said opener is integrally formed with said housing.

17. The test device according to claim 16, wherein:
said opener is integrally formed with said housing and connected via breakaway portions of said housing which, when broken, permanently sever said opener from said housing.

18. The test device according to claim 1, wherein:
said opener is coupled to said housing by a snap fit coupling.

19. The test device according to claim 1, wherein:
said housing includes at least one barb or spike disposed under said sealed reservoir, said barb or spike constructed to pierce and causes said sealed reservoir to drain the solution when said opener is in said second position.

20. A test device for use with a solution and for use with a conjugate having a marker, the test device for determining the presence of a ligand in a liquid sample, the test device comprising:
   a) a first sorbent strip having a first location for receiving the solution and defining a first migration path for the solution and the conjugate;
   b) a second sorbent strip distinct from said first sorbent strip having a second location for receiving the liquid sample and defining a second migration path for the sample distinct from said first migration path; and c) a test site located on or in at least one of said first sorbent strip or said second sorbent strip, said test site having an immobilized ligand-binding mechanism, said first and second sorbent strips touching each other at the test site, and said second migration path extending laterally from said second location to at least said test site;

d) a housing that houses said first and second sorbent strips, said housing defining a first opening aligned with said first location, a second opening aligned with said second location, and a window aligned with said test site and through which said test site is viewable;

e) a sealed reservoir filled with the solution, said sealed reservoir disposed in alignment with said first opening and coupled to said housing; and f) an opener coupled to said housing, said opener arranged to rotate from a first position in which the opener is not in contact with said sealed reservoir and to rotate to a second position in which the opener causes said sealed reservoir to effect a release of the solution from said reservoir and into said first opening and onto said first sorbent strip.

21. A method of using a test device with a liquid solution, the method comprising:

a) providing a test device comprising:
i) a housing that houses a plurality of sorbent strips, at least one strip having a location for receiving the solution, said housing defining at least an opening aligned above said location for receiving the solution,
ii) a sealed reservoir filled with the liquid solution, said reservoir being disposed in alignment with said opening and coupled to said housing, and
iii) an opener coupled to said housing, said opener arranged to rotate from a first position, in which said opener is not in contact with said sealed reservoir, to a second position, in which said opener causes said sealed reservoir to effect a release of the solution from said reservoir and into said opening and onto said sorbent strip housed within said housing; and b) rotating said opener from said first position to said second position to effect a release of the solution from said reservoir and into said opening and onto said sorbent strip housed within said housing.

* * * * *